(12) United States Patent
Sasai et al.

(10) Patent No.: US 8,521,561 B2
(45) Date of Patent: Aug. 27, 2013

(54) DATABASE SYSTEM, PROGRAM, IMAGE RETRIEVING METHOD, AND REPORT RETRIEVING METHOD

(75) Inventors: Kosuke Sasai, Kobe (JP); Youichi Kawakami, Osaka (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 1459 days.

(21) Appl. No.: 11/895,042

(22) Filed: Aug. 22, 2007

(65) Prior Publication Data

US 2008/0052126 A1 Feb. 28, 2008

(30) Foreign Application Priority Data

Aug. 25, 2006 (JP) ................................ 2006-228968

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | | |
|---|---|---|---|---|
| 5,272,625 A | * | 12/1993 | Nishihara et al. | 1/1 |
| 6,609,135 B1 | * | 8/2003 | Omori et al. | 1/1 |
| 7,676,381 B2 | * | 3/2010 | Kawakami et al. | 705/2 |
| 7,684,071 B2 | * | 3/2010 | Moriwaki | 358/1.15 |
| 7,743,054 B2 | * | 6/2010 | Sasai | 707/721 |
| 2001/0051881 A1 | * | 12/2001 | Filler | 705/3 |

FOREIGN PATENT DOCUMENTS

| | | |
|---|---|---|
| JP | 2000-298606 | 10/2000 |
| JP | 2001-134589 | 5/2001 |
| JP | 2002-175298 | 6/2002 |
| JP | 2002-259410 | 9/2002 |
| JP | 2005-100090 | 4/2005 |

* cited by examiner

*Primary Examiner* — Michael Fuelling
(74) *Attorney, Agent, or Firm* — Brinks Hofer Gilson & Lione

(57) ABSTRACT

In a plurality of pieces of single report structured data that is stored in a structured database in a diagnosis information database, character information constructing a radiological report describing detailed information of image data is added as metadata for search to the image data. For example, only by designating image data to be read as image (retrieval reference image) data as a reference of retrieval by a reading physician as the user during radiological operation, the character information already added to the retrieval reference image data is set as a keyword. By a keyword search using the metadata, data of a similar image and a related report of the retrieval reference image data are detected from the structured DB.

12 Claims, 24 Drawing Sheets

F I G. 1
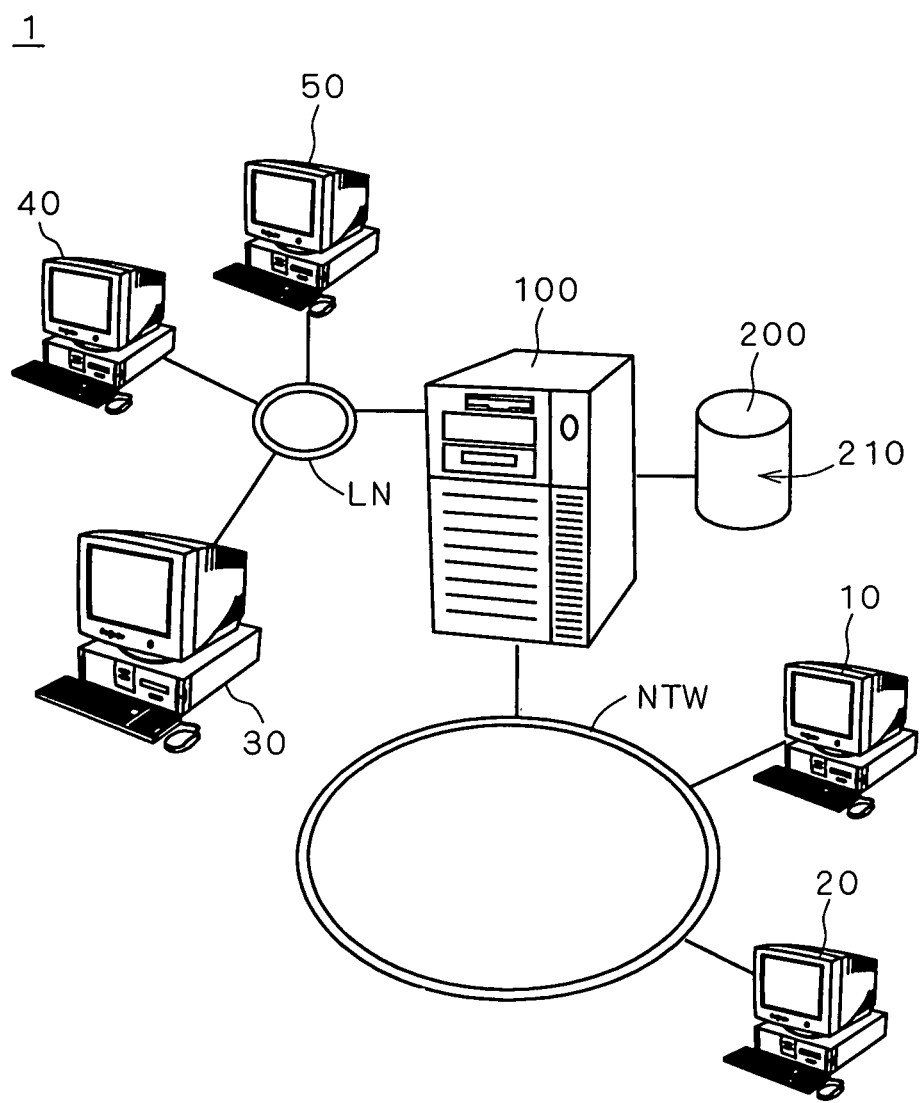

FIG. 10

| PATIENT'S ID | PATIENT'S NAME | BIRTHDAY | AGE | SEX | STATE | TEST ID | TEST DATE | TEST REGION | MODALITY | THE NUMBER OF IMAGES |
|---|---|---|---|---|---|---|---|---|---|---|
| 20060001 | TARO YAMADA | 1946.06.03 | 49.02 | F | NOT READ YET | hyo-1-593820-5-20020603-173737 | 2002.06.03 | SKULL | CR | 2 |
| 20060001 | HANAKO TANAKA | 1946.06.03 | 49.02 | F | READING | hyo-1-593820-5-20020603-173737 | 2002.06.03 | CHEST | CR | 3 |
| 20060001 | HANAKO TANAKA | 1946.06.03 | 49.02 | F | PENDING APPROVAL | hyo-1-593820-5-20020603-173737 | 2002.06.03 | CHEST | CT | 160 |
| 20060001 | HANAKO TANAKA | 1946.06.03 | 49.02 | F | READING | hyo-1-593820-5-20020603-173737 | 2002.06.03 | CHEST | CT | 160 |
| 20060001 | HANAKO TANAKA | 1946.06.03 | 49.02 | F | NOT READ YET | hyo-1-593820-5-20020603-173737 | 2002.06.03 | CHEST | CT | 160 |
| 20060001 | HANAKO TANAKA | 1946.06.03 | 49.02 | F | READING | hyo-1-593820-5-20020603-173737 | 2002.06.03 | CHEST | CT | 160 |

FIG. 12

| ■ REQUESTED MATTER |
|---|
| 20S, MALE.<br>STUBBORN COUGH.<br>PLEASE MAKE DETAILED<br>CHECK WITH CHEST CR. |

FIG. 13

| ■ DETAILS OF TEST | |
|---|---|
| ATTRIBUTES | VALUES |
| MODALITY | CR |
| NAME OF DOCTOR AS REPORT GENERATOR | TARO TOKKYO |
| DATE AND TIME OF REPORT GENERATION | JANUARY, 2005 |
| THE NUMBER OF IMAGES | 2 |
| PATIENT'S NAME | HANAKO TOKKYO |
| PATIENT'S SEX | F |

FIG. 14

| ■ FREQUENTLY-APPEARING WORD INPUT |
|---|
| bilateral apical pleural thickening<br>aortic calcification<br>aortic elongation<br>mild cardiomegaly<br>Scoliosis<br>BHL |

FIG. 15

■ SUMMARY INPUT

THERE IS NO PARTICULAR FINDING.
NO ABNORMAL SHADOW IS SEEN.
NO CHANGE FROM PREVIOUS TIME (//**)
AFTER VALVE REPLACEMENT.
PLEASE FOLLOW UP AFTER 3 MONTHS.
PLEASE MAKE DETAILED CHECK WITH CT.

■ REPORT GENERATION

MODALITY : CR—TEST REGION : CHEST

■→ SELECT CATEGORY.

LUNG → SOFT PART →
MEDIASTINAL SPACE → PLEURAL MEMBRANES (MARGINAL) →
BONE → OTHERS →

| | | | |
|---|---|---|---|
| Pf1 | AGE | 53 | Pv1 |
| Pf2 | SEX | MALE | Pv2 |
| Pf3 | MODALITY | MR | Pv3 |
| Pf4 | TEST REGION | SKULL | Pv4 |
| Pf5 | IMAGING PARAMETER | T2WI | Pv5 |
| Pf6 | REGION | FRONTAL LOBE | Pv6 |
| Pf7 | BASIC FINDING | HIGH SIGNAL AREA | Pv7 |
| Pf8 | FEATURE | LIGHT | Pv8 |

FIG. 22

| COMBINATION OF SYNONYM AND RELATED WORD |
|---|
| OBSOLTE BRAIN INFARCTION, OLD BRAIN INFARCTION |
| T2WI, T2WI-WEIGHTED IMAGE, T2WI IMAGE |
| ⋮ |

FIG. 23

■ SIMILAR IMAGES 1 ■

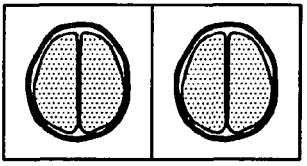

48 YEARS OLD
FEMALE
S K U L L , M R

HIGH SIGNAL AREA IS SEEN IN FRONTAL LOBE AND OCCIPITAL LOBE IN T2WI-WEIGHTED IMAGES. OLD BRAIN INFARCTION IS SUSPECTED.

■ SIMILAR IMAGES 2 ■

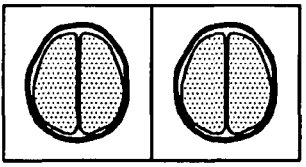

68 YEARS OLD
MALE
S K U L L , M R

LIGHT HIGHT SIGNAL AREA IS SEEN IN FRONTAL LOBE AND RIGHT TEMPORAL LOBE IN T2WI.
DETAILED TEST WITH CT IS REQUIRED.

FIG. 24

MARK CHECK BOX FOR ATTRIBUTE USED FOR SEARCH

☐ AGE
  -( ) TO +( )
☐ SEX
■ MODALITY
■ TEST REGION

■ IMAGING PARAMETER
■ REGION
■ BASIC FINDING
☐ FEATURE
☐ DIAGNOSIS ( CLEAR )   ( DETERMINE )
                        — MP

FIG. 27
| ■ RELATED IMAGES 1 ■ | |
|---|---|
| 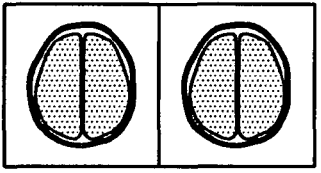<br>53 YEARS OLD<br>MALE<br>S K U L L , M R | NO REMARKABLE CHANGE IS SEEN IN HIGH SIGNAL AREA OF FRONTAL LOBE FROM LAST TIME. |
| ■ RELATED IMAGES 2 ■ | |
|---|---|
| 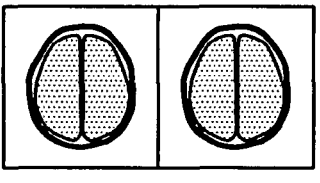<br>53 YEARS OLD<br>MALE<br>S K U L L , M R | LIGHT HIGH SIGNAL AREA IS SEEN IN FRONTAL LOBE IN T2WI.<br>LACUNAR INFARCTION IS SUSPECTED. |

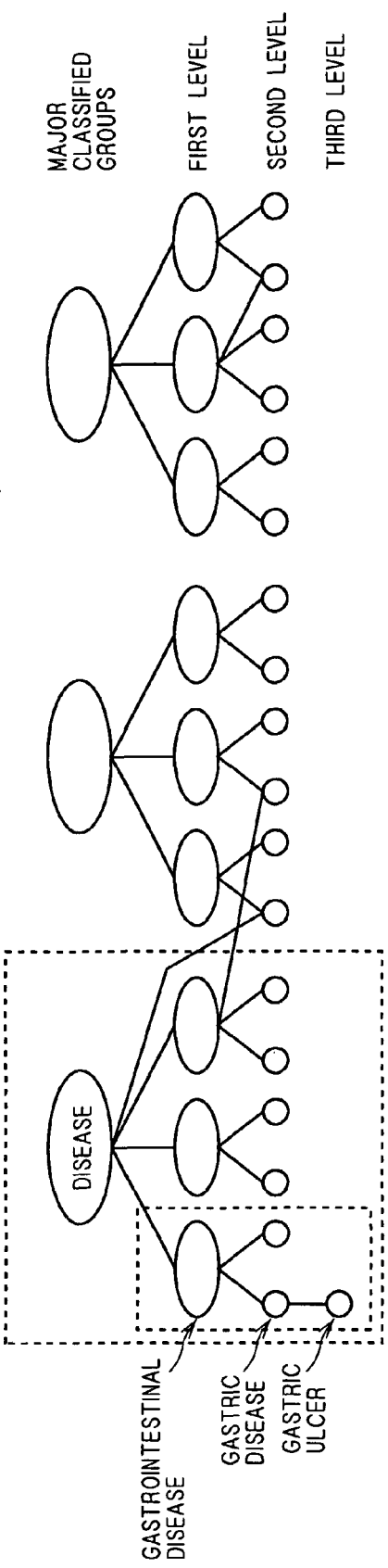

F I G . 2 9
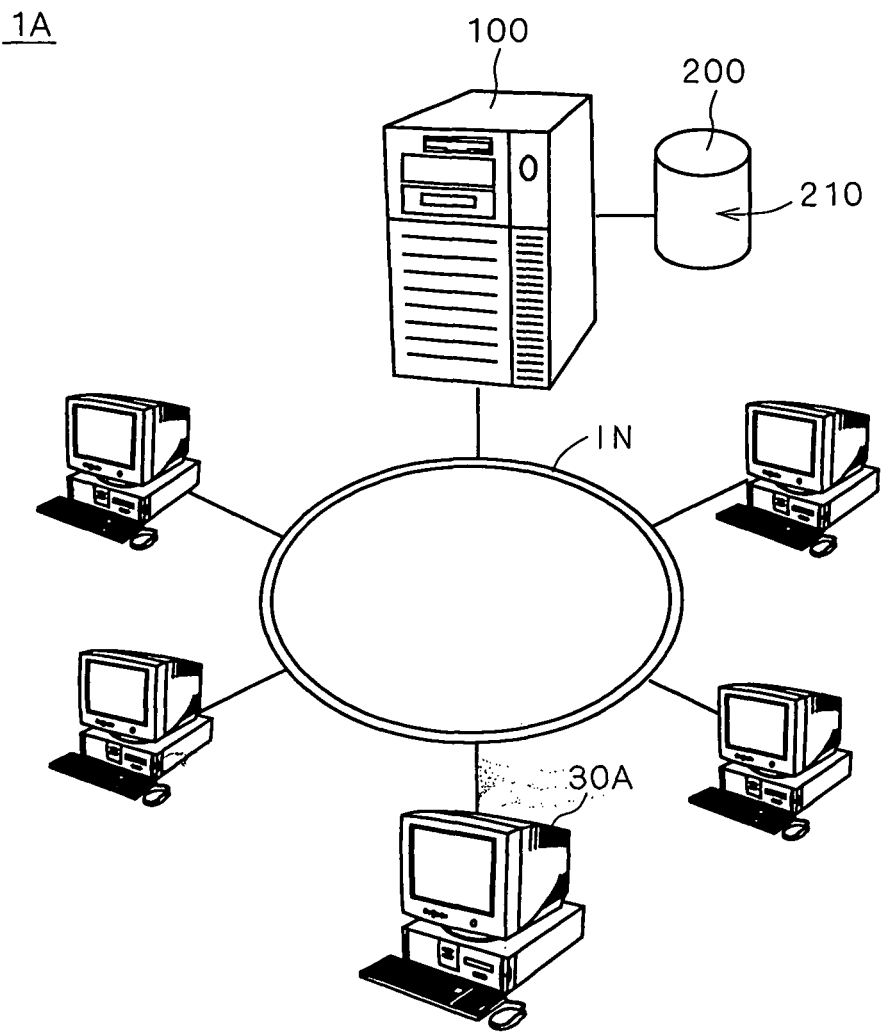

F I G . 3 1
DG1
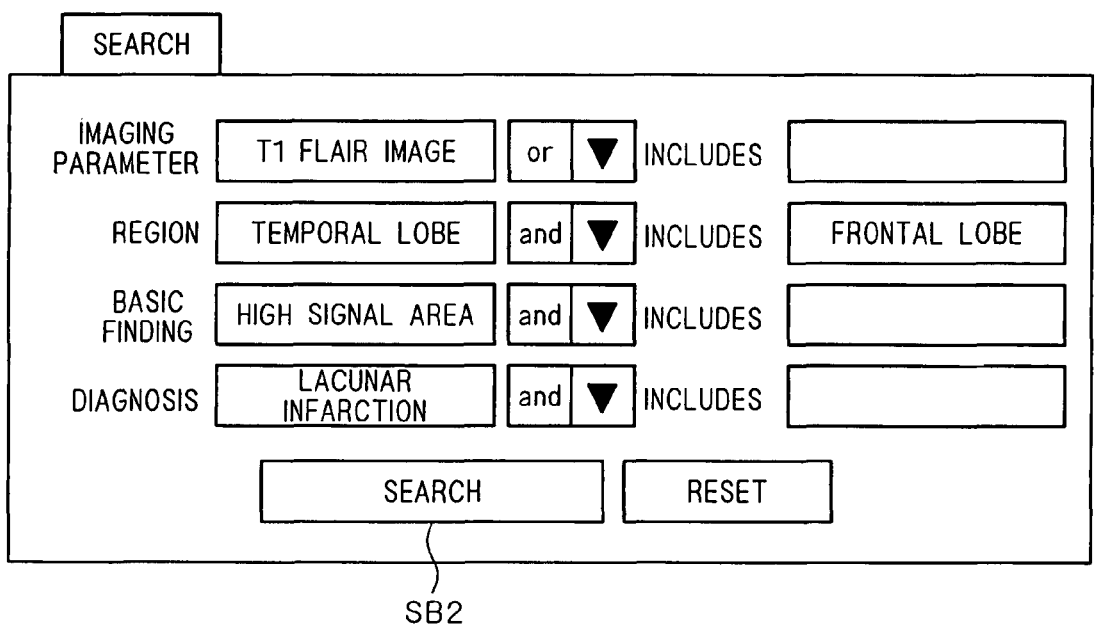

FIG. 32

DATABASE SYSTEM, PROGRAM, IMAGE RETRIEVING METHOD, AND REPORT RETRIEVING METHOD

This application is based on application No. 2006-228968 filed in Japan, the contents of which are hereby incorporated by reference.

BACKGROUND OF THE INVENTION

1. Field of the Invention

The present invention relates to an information retrieving process technique.

2. Description of the Background Art

In the medical field, the technique of forming a number of radiological reports as electronic data and storing the electronic data in a database system such as PACS (Picture Archiving and Communication System) is being spread. In the database system, the radiological report formed as electronic data and image data as an object of reading is stored so as to be associated with each other.

In a scene of obtaining a reference material at the time of diagnosis or generating data of representative cases, if similar images or radiological reports in the past can be retrieved on the basis of a certain image, it is very useful.

As a conventional technique of retrieving similar images on the basis of a certain image, a retrieval technique using a feature amount of an image is known. The technique, however, has a problem of low retrieval precision.

Other techniques are also proposed such as a technique of retrieving similar images by using both a feature amount of an image and metadata given to the image (for example, Japanese Patent Application Laid-Open Nos. 2002-259410 and 2005-100090), a technique for simply giving metadata to an image (for example, Japanese Patent Application Laid-Open Nos. 2000-298606 and 2002-175298), and a technique of retrieving a moving image in accordance with similarity of dynamic metadata (dynamic feature amount) (for example, Japanese Patent Application Laid-Open No. 2001-134589).

In the technique of Japanese Patent Application Laid-Open Nos. 2002-259410 and 2005-100090, however, a troublesome work of giving, metadata to an image is necessary. In the technique of Japanese Patent Application Laid-Open No. 2000-298606, although proper metadata can be selected from prepared options of metadata, the troublesome work of giving metadata is still necessary, the kinds of metadata which can be given are limited, and it is not flexible. In the technique of Japanese Patent Application Laid-Open No. 2002-175298, metadata has to be entered before the metadata is registered as binary data, and the troublesome work of giving metadata is necessary. Further, in the technique of Japanese Patent Application Laid-Open No. 2001-134589, it is very troublesome to enter retrieval parameters at the time of performing retrieval using metadata.

SUMMARY OF THE INVENTION

The present invention is directed to a database system.

According to the present invention, the database system includes: an association information database that stores, report by report, association information in which a plurality of pieces of character information constructing a report and one or more pieces of image data related to the report are associated with each other; an image designating unit, in response to an operation of a user, for designating one or more pieces of image data associated with one or more pieces of character information belonging to at least part of a predetermined number of classification items to which the plurality of pieces of character information belong; and an image detecting unit for detecting one or more pieces of image data different from but similar to the one or more pieces of image data designated by the image designating unit by performing a keyword search using a search keyword group formed by one or more pieces of character information associated with one or more pieces of image data designated by the image designating unit, and using, as metadata for data retrieval, the plurality of pieces of character information associated with image data in the association information database.

Since the character information constructing a report describing detailed information of an image is added as metadata to the image report by report and a keyword search using the metadata can be performed by using, as a keyword, the character information added to an image only by designating the image, the retrieving technique realizing high image retrieval precision and easy entry of a search condition can be provided.

According to another aspect of the present invention, the database system includes: an association information database that stores, report by report, association information in which a plurality of pieces of character information constructing a report and one or more pieces of image data related to the report are associated with each other; an image designating unit, in response to an operation of a user, for designating one or more pieces of image data associated with one or more pieces of character information belonging to at least part of a predetermined number of classification items to which the plurality of pieces of character information belong; and a report detecting unit for detecting one or more pieces of report data related to the one or more pieces of image data designated by the image designating unit by performing a keyword search using a search keyword group formed by one or more pieces of character information associated with one or more pieces of image data designated by the image designating unit, and using, as metadata for data retrieval, the plurality of pieces of character information associated with image data in the association information database.

Since the character information constructing a report describing detailed information of an image is added as metadata to the image report by report and a keyword search using the metadata can be performed by using, as a keyword, the character information added to an image only by designating the image, the retrieving technique realizing high report retrieval precision and easy entry of a search condition can be provided.

The present invention is also directed to a computer software product including a recording medium that records a computer-readable software program for making a computer operate as a database system.

The present invention is also directed to an image retrieving method.

The present invention is also directed to a report retrieving method.

Therefore, an object of the present invention is to provide a technique realizing high precision of retrieval of an image and a report, easy addition of metadata to an image, and easy entry of a search condition.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram showing outline of a database system according to an embodiment of the present invention;

FIG. 10 is a diagram illustrating a test list screen;

FIG. 12 is a diagram showing a requested matter displayed in a requested matter display area;

FIG. 13 is a diagram illustrating the details of a test displayed in a test information display area;

FIG. 14 is a diagram illustrating a list of frequently-appearing phrases;

FIG. 15 is a diagram illustrating a list of summaries;

FIG. 16 is a diagram illustrating information acquisition condition determination template display;

FIG. 21 is a diagram showing character information expressing features of a retrieval reference image;

FIG. 22 is a diagram showing data stored in a dictionary DB;

FIG. 23 is a diagram showing a retrieval result screen of similar images and relation reports;

FIG. 24 is a diagram illustrating a setting screen for customizing retrieval conditions;

FIG. 27 is a diagram illustrating a related-image display screen;

FIG. 28 is a diagram for explaining the details of thesaurus;

FIG. 29 is a diagram showing outline of a database system in the modification;

FIG. 31 is a diagram illustrating dialog for determining a retrieval condition in the modification;

FIG. 32 is a diagram illustrating a retrieval result screen of images and remarks in the modification.

DESCRIPTION OF THE PREFERRED EMBODIMENTS

Figure 2:
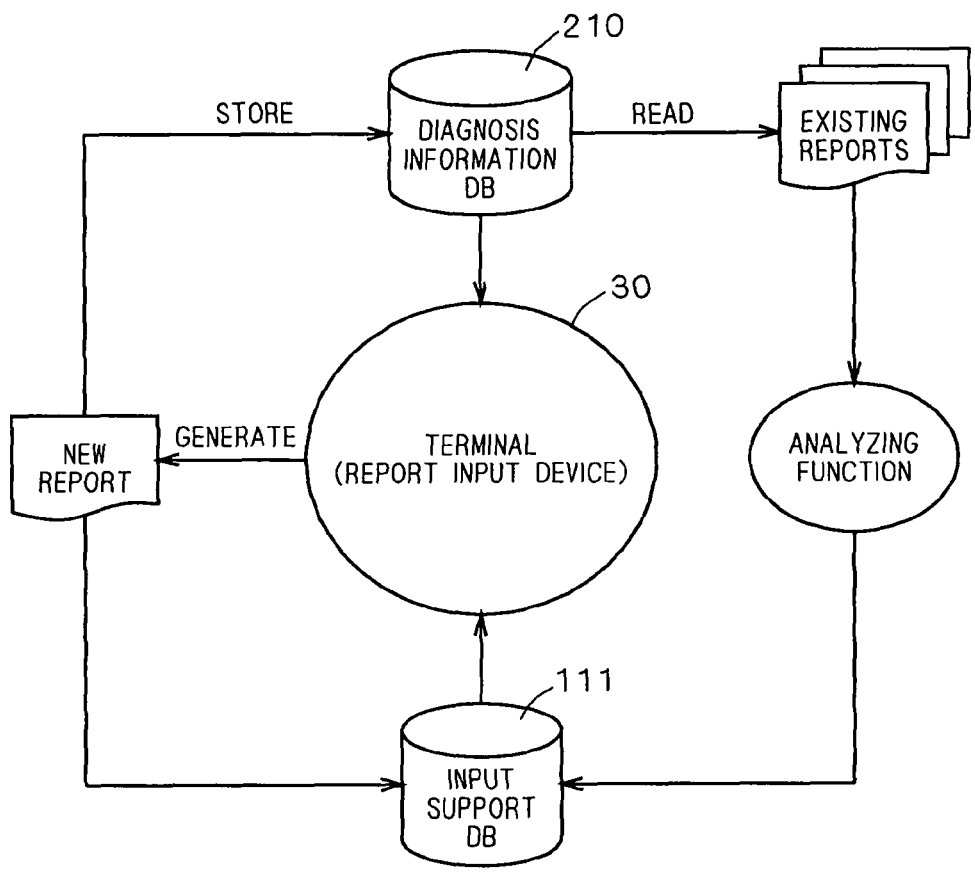
FIG. 2 is a diagram showing outline of information process related to an input support function.

Embodiments of the present invention will be described hereinafter with reference to the drawings.

Outline of Database System

A database system as an embodiment of the present invention is a system for reporting a result of interpreting an image such as a radiologic image. The image is usually stored in an image server of a PACS (Picture Archiving and Communication System). There is also a database for storing radiological reports about images (report database). The report database (report DB) may exist in a server in the PACS or another server out of the PACS.

FIG. 1 is a diagram showing outline of a database system 1 as an embodiment of the invention.

The database system 1 is, for example, a system for controlling and processing diagnosis information in a hospital. In the system 1, a server 100 and terminal devices, such as terminals 10 and 20, are connected to a network line NTW such as LAN so that data can be transmitted/received to/from each other. To the server 100, a storing unit 200 is connected so that data can be transmitted/received and, further, terminal devices, such as terminals 30, 40, and 50, are connected via a network line LN so that data can be transmitted/received.

The storing unit 200 stores a diagnosis information database (diagnosis information DB) 210 for storing medical information (hereinafter, also called "diagnosis information") of a number of patients to be diagnosed.

In the diagnosis information DB 210, an image database (image DB), a report database (report DB), and a structured database (structured DB) are stored. In the image DB, a plurality of pieces of image data obtained by image capturing with a radiation ray in the department of radiology on patients are stored. In the report DB, data obtained by associating one or more pieces of image data stored in the image DB with data indicative of radiological reports described for the one or more pieces of image data for each of a plurality of radiological reports (hereinafter, also called "report data with image" or simply "report data") is stored. In the structured DB, data obtained by structuring the report data with an image (single report structured data) stored in the report DB is stored.

The image data associated in a single piece of report data with an image is not limited to one frame, but image data of one frame or more, for example, two or more frames may be employed. In the report data with images, data of a natural sentence and various character information constructing a radiological report and information specifying the location of the image data (for example, description of a file name or URI) is associated with each other.

To each piece of the image data stored in the image DB, information of attributes of DICOM (Digital Image and Communications in Medicine) (DICOM attributes) is added. The attribute information includes, for example, information indicative of patient ID, age, sex, modality, a region to be tested, a reading physician, and a primary doctor. A configuration in which at least one piece of the seven pieces of information is included may be employed.

In the diagnosis information DB 210, information (test list information) of a list of tests conducted on a number of patients (test list) is stored. The test list information includes, for example, a list of the information of the DICOM attributes added to image data on the test unit basis. More specifically, the test list information includes, for example, information indicative of attributes of a patient who had a test (patient ID, patient name, birthday, age, and sex), a state showing whether a radiological report was generated or not, a test ID specifying the test, test date, a region to be tested, a modality indicative of imaging parameters, and the number of images taken. In the diagnosis information DB 210, attribute information such as an ordered matter (requested matter) from a primary doctor and the details of a test (information on the patients and tests) is stored so as to be associated with the test ID.

The server 100 writes/reads various information to/from the diagnosis information DB 210 and performs an information process based on the various information stored in the diagnosis information DB 210. The information process in the server 100 is properly controlled by a data control function provided for the terminals 10 to 50.

In the database system 1, for example, the terminals 10 and 20 are terminals used by primary doctors of patients, the terminal 30 is a terminal (report input device) for inputting a radiological report by a reading physician of a radiology department, and the terminals 40 and 50 are terminals used by technologists of the radiology department.

When an order is entered from the terminals 10 and 20 to the terminals 40 and 50 of the radiology department, the technologist of the radiology department obtains image data of an affected area by using an MR apparatus, a CR apparatus, or the like. The image data of the affected area is stored from the terminals 40 and 50 to the diagnosis information DB 210 via the server 100. After that, the doctor of the radiology department inputs a radiological report by the report input device 30 with reference to a screen on which the image data stored in the diagnosis information DB 210 is visibly output.

The server 100 generates information (input support information) for supporting input of a new radiological report by using radiological reports (existing radiological reports) already stored in the diagnosis information DB 210, obtains (extracts) necessary information from the input support information, and provides the extracted information in the form of a template display to the report input device 30.

The server 100 also forms a structured DB in the diagnosis information DB 210 by structuring the report data with images stored in the report DB. At the time of inputting a new radiological report by via an image designating unit that includes the report input device 30, by using the structured DB, the server 100 retrieves and provides, as reference information, image data similar to image data designated by the report input device 30 and data of a radiological report related to the image data designated by the report input device 30 (for example, a remark constructing part of the radiological report) to the report input device 30. The structured DB plays the role of information supporting retrieval (retrieval support information).

The function of supporting input of a new radiological report in the server 100 will be called an "input support function" hereinafter. The input support function includes a function (retrieval function) of retrieving data of an image (similar image) similar to image data designated by the user and data of a radiological report related to the image data designated by the user (related report). The input support function including the retrieval function will be described more specifically later.

Figure 3:
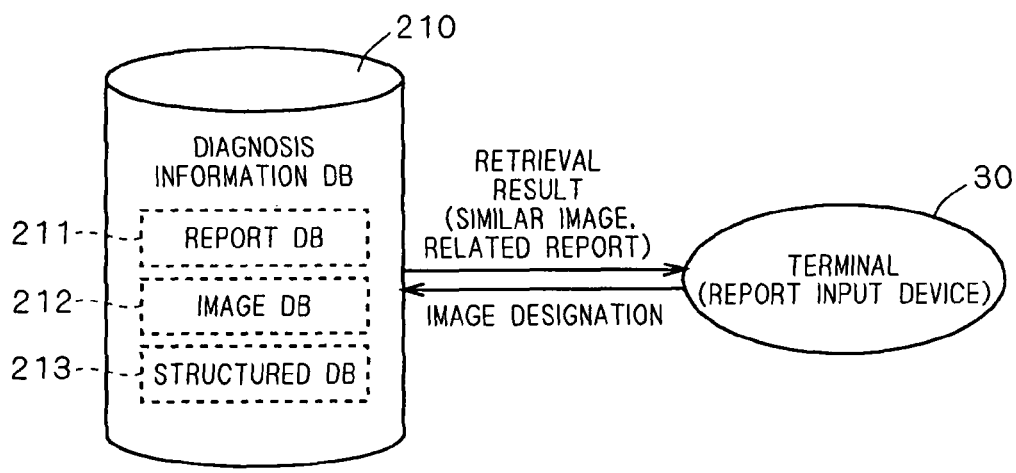
FIG. 3 is a diagram showing outline of information process related to a retrieval function.

FIGS. 2 and 3 are diagrams showing outline of information processes related to the input support function in the database system 1. FIG. 3 is a diagram paying attention to the outline of the information processes related to the retrieval function.

In the diagnosis information DB 210, data indicative of a captured image and a generated radiological report is stored. As shown in FIG. 2, the report input device 30 is a device of obtaining image data to be interpreted from the diagnosis information DB 210 and creating data indicative of a radiological report. The server 100 reads the data indicative of an existing radiological report from the diagnosis information DB 210 and analyzes it by the analyzing function, thereby creating information supporting generation and input of a radiological report (input support information). The created information is stored in an input support DB 111. In the report input device 30, a new radiological report is input by using the input support information. Data indicative of a newly created radiological report is added to the diagnosis information DB 210 and used for reinforcing the input support information stored in the input support DB 111.

As shown in FIG. 3, the diagnosis information DB 210 includes a report DB 211 storing a number of pieces of report data with images, an image DB 212 storing a number of pieces of image data of affected areas, and a structured DB 213 storing single report structured data obtained by structuring the report data with images stored in the report DB 211. The report input device 30 can obtain, as a retrieval result, image data similar to designated image data and data of a radiological report related to designated image data from the diagnosis information DB 210. Data indicative of a new radiological report input from the report input device 30 is also used for reinforcing the report DB 211 and the structured DB 213.

Figure 4:
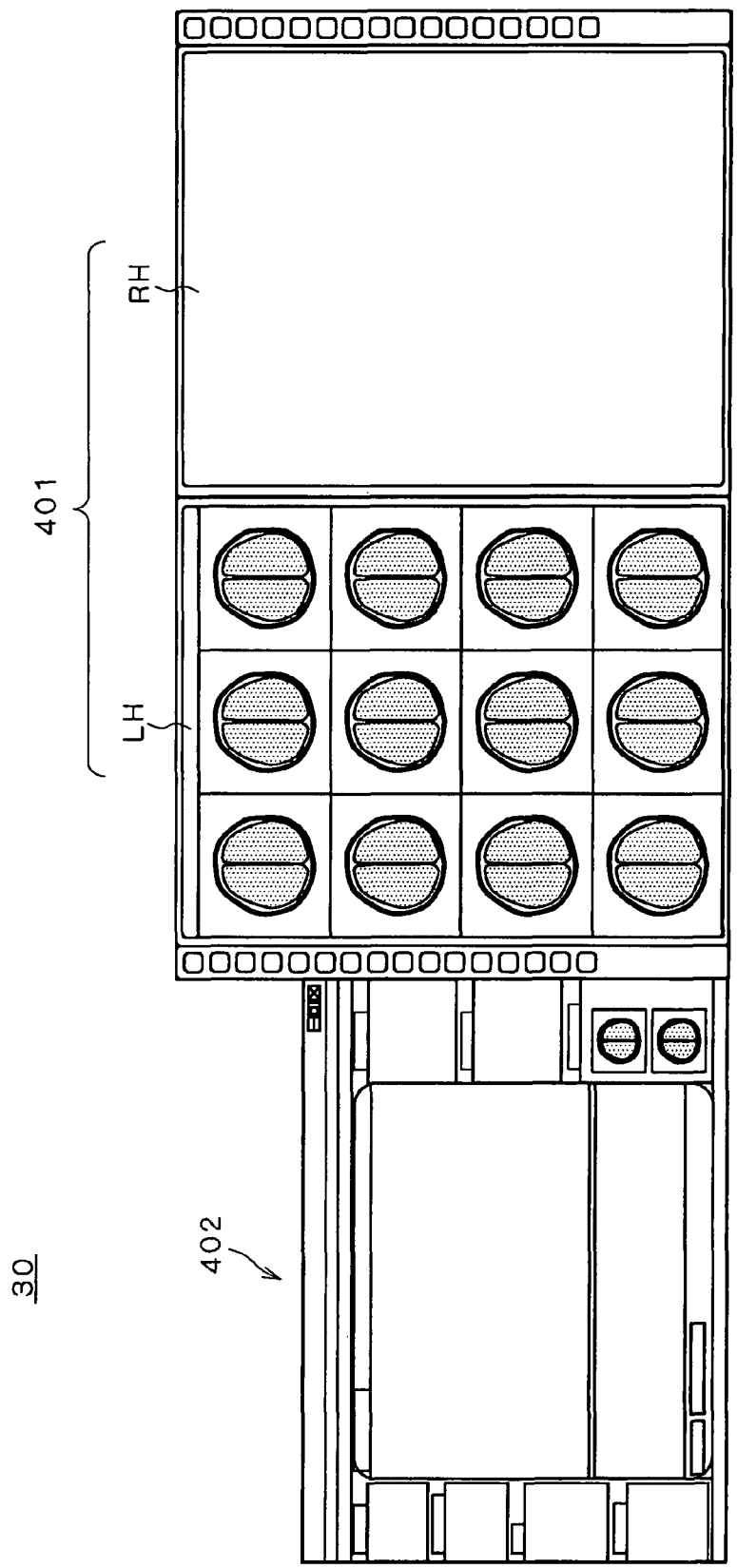
FIG. 4 is a diagram showing a state of inputting a new radiological report by a report input device.

FIG. 4 is a diagram illustrating a state where a new radiological report is entered in the report input device 30. As shown in FIG. 4, in the report input device 30, a reading physician in the radiology department enters a new radiological report on an input screen 402 by properly referring to a screen (image display screen) 401 on which image data of a patient stored in the diagnosis information DB 210 is visibly output. In FIG. 4, image data is visibly output to a display area LH of the left half of the image display screen 401, and image data is not visibly output to a display area RH of the right half. The display area RH functions as an area for displaying various retrieval results in the retrieval function.

Input Support Function

The input support function has a function of creating input support information by extracting elements necessary for entering a new radiological report from a number of pieces of report data with images using the number of pieces of report data with images stored in the diagnosis information DB 210 as past knowledge, and structuring the elements by using the RDF (Resource Description Framework) or the like, and properly displaying the created input support information. The input support function also includes a function of performing retrieval using the retrieval support information (in this case, the structured DB 213).

Operations realized by the input support function are mainly four operations: an operation (support information creating operation) for generating retrieval support information; an operation (test selecting operation) of selecting a test corresponding to a new radiological report to be input; an operation (input supporting operation) for actually supporting entry of a new radiological report on the basis of the input support information; and an operation (retrieving operation) realized by the retrieval function.

Functional Configuration

Figure 5:
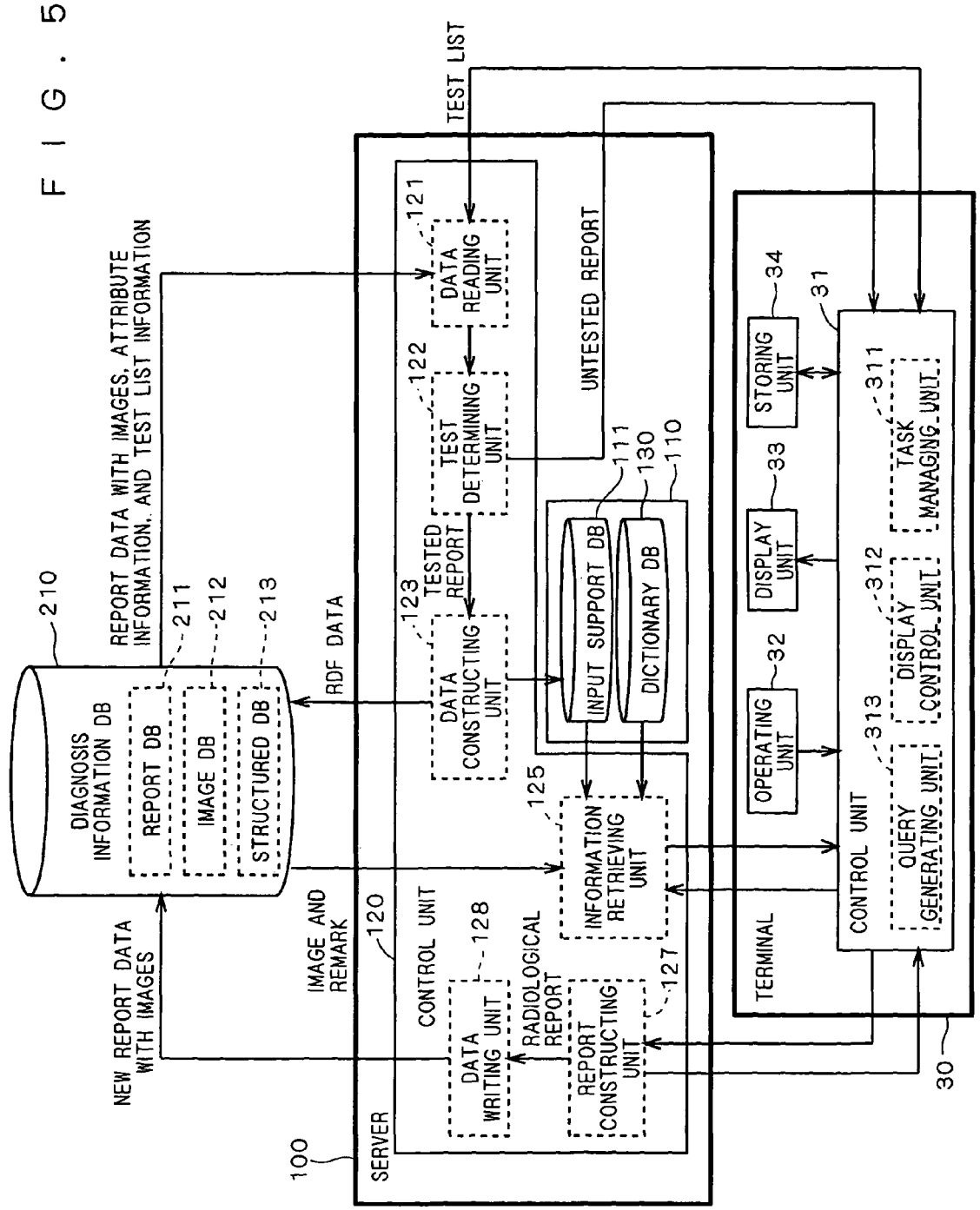
FIG. 5 is a block diagram showing a functional configuration related to entry of a new report and information retrieval.

FIG. 5 is a block diagram showing the input support function including the retrieval function in the database system 1 and a functional configuration related to input of a new radiological report by using the input support function. In the functional configuration shown in FIG. 5, the function of control units 120 and 31 is a conceptual function realized by executing a program stored in storing units 110 and 34 such as a hard disk by a CPU or the like in the server 100 and the terminal (report input device) 30. Various data temporarily generated in various information processes executed by the functional configuration is temporarily stored in, for example, a RAM or the like provided in the control units 120 and 31.

The server 100 includes, mainly the storing unit 110 and the control unit 120.

The storing unit 110 stores various programs and various data for realizing various controls, functions, and the like in the server 100. For example, the storing unit 110 stores the input support DB 111 and a dictionary database (dictionary DB) 130.

The input support DB 111 stores input support information created by the support information creating operation. The details of the input support information will be described concretely later.

The dictionary DB 130 is a database storing character information such as words and phrases so as to be associated with words and the like having the same meaning, similar meaning, and related meaning as the character information. That is, in the dictionary DB 130, character information such as words having predetermined relations such as synonyms, equivalent terms, and related terms is associated with each other. In other words, in the dictionary DB 130, one or more pieces of character information (related character information) having a predetermined relation are associated with each piece of at least one or more pieces of character information. In the dictionary DB 130, a term having one or more relations out of synonym, equivalent term, and related term may be associated.

The control unit 120 controls various control, functions, and the like of the server 100 in a centralized manner and includes, as functions, a data reading unit 121, a test determining unit 122, a data constructing unit 123, an information retrieving unit 125, a report constructing unit 127, and a data writing unit 128.

The data reading unit 121 reads, from the diagnosis information DB 210, report data with an image, attribute information corresponding to image data of the report data with an image, and test list information. The data reading unit 121 transmits the report data with an image, attribute information, and test list information to the test determining unit 122 in the support information creating operation and the input supporting operation, and transmits the test list information to the control unit 31 in the report input device 30 in the test selecting operation.

The test determining unit 122 determines whether or not a radiological report is generated by writing a remark or the like on a radiological report of each test with reference to the test list information. The test determining unit 122 transmits the created (that is, tested) report data with an image together with the attribute information to the data constructing unit 123 in the support information creating operation. The test determining unit 122 transmits uncompleted (that is, untested) report data with an image together with the attribute information to the control unit 31 in the report input device 30 in the input supporting operation.

With respect to a plurality of pieces of report data with images, a storage controlling unit, such as the data constructing unit 123, extracts necessary elements from remarks as a natural sentence in a radiological report expressed by report data with an image, extracts various elements included in the attribute information, and structures the elements by using the RDF, thereby creating the input support information and constructing the input support DB 111 and thereby creating retrieval support information and constructing the structured DB 213.

The input support information generated here is information (hereinafter, also called "element network information") including information (hereinafter, also called "network information") in which elements belonging to items of a plurality of elements (in this case, character information) constructing a remark are associated with each other between the items like in a network.

The retrieval support information generated here is a database (structured DB 213) constructed by storing, for each of a plurality of reports, information (hereinafter, also called "association information") in which a plurality of pieces of character information (for example, phrases) constructing a remark of a report and one or more pieces of image data to be interpreted in the report are associated with each other. The structured DB 213 is also called a association information database (DB).

The information retrieving unit 125 obtains a part of the network information (hereinafter, also called "partial network information") from the element network information stored in the input support DB 111 in order to construct template display for directly supporting input of a radiological report in response to a request from the report input device 30. The information retrieving unit 125 generates data (network display screen data) of a display screen including a list of the partial network information in which elements belonging to the items of the plurality of elements are associated with each other between the items on the basis of the partial network information and outputs the generated data to the control unit 31, which with the report input device 30 forms part of the image designating unit.

The information retrieving unit 125 retrieves the structured DB 213 for data of a similar image and a related report of image data designated in the report input device 30, generates data of a screen displaying the retrieval result (retrieval result display screen data), and outputs the data to the control unit 31. In the retrieving operation, using one or more pieces of character information associated with the designated one or more pieces of image data as a retrieval keyword, a plurality of pieces of character information associated with the image data in the structured DB 213 are regarded as metadata for data retrieval added to the image data. A retrieving process (that is, a keyword retrieving process) for determining whether the metadata and the retrieval keyword match each other or not is performed.

The report constructing unit 127 receives new single report structured data which is input from the control unit 31 in the form of structured data in accordance with an operation of an operating unit 32 of the user and, on the basis of the single report structured data, generates new report data with an image according to a predetermined rule.

The data writing unit 128 adds the report data with an image generated by the report constructing unit 127 to the report DB 211 in the diagnosis information DB 210. In this case, the new single report structured data which is input to the report constructing unit 127 is added as it is also to the structured DB 213 in the diagnosis information DB 210. Further, the new single report structured data which is input to the report constructing unit 127 is transmitted as it is to the data constructing unit 123 and is also used for updating of the input support DB 111.

The report input device 30 mainly has the control unit 31, the operating unit 32, a display unit 33, and the storing unit 34.

The control unit 31 controls the various controls, functions, and the like of the report input device 30 and has, as functions, a task managing unit 311, a display control unit 312, and a query generating unit 313.

When a test whose new radiological report is to be input (report input target test) is selected, the task managing unit 311 specifies a task related to generation of new report data with an image corresponding to the report input target test.

The display control unit 312 visibly outputs various screens on the display unit 33 on the basis of various information and the like input from the server 100. For example, the display control unit 312 visibly outputs a network display screen on the display unit 33 on the basis of the network display screen data input from the information retrieving unit 125 and visibly outputs a retrieval result display screen on the display unit 33 on the basis of the retrieval result display screen data.

The query generating unit 313 generates a query using, as a retrieval keyword, character information associated with the designated image data by various operations on the operating unit 32 performed by the reading physician as the user, and outputs the query to the information retrieving unit 125.

The operating unit 32 is constructed by including a keyboard, a mouse, and the like and, when properly operated by the user, outputs various signals to the control unit 31.

The display unit 33 is constructed by any of various displays such as a liquid crystal display and visibly outputs, for example, network display screen data and retrieval result display screen data generated in the information retrieving unit 125 in accordance with control of the display control unit 312.

The storing unit 34 stores various programs and various data for realizing various controls, various functions, and the like in the report input device 30.

With reference to FIG. 5, the support information creating operation, test selecting operation, input supporting operation, and retrieving operation as the main four operations realized by the input support function will be described one by one.

Support Information Creating Operation

First, the data reading unit 121 reads report data with an image, attribute information corresponding to the report data with an image, and test list information and transmits the information to the test determining unit 122. The test determining unit 122 determines whether report data with an image is generated for a test or not by referring to the test list information, and transmits the generated report data with an image together with the attribute information to the data constructing unit 123. The data constructing unit 123 extracts necessary elements from a remark as a natural sentence in a radiological report and also various elements included in the attribute information, and structures the elements by using the RDF. The structuring of report data with an image is realized by using, for example, machine learning.

The machine learning and structuring of report data with an image in the data constructing unit 123 will be described below.

First, for example, a corpus for learning or the like is given as teaching data, thereby learning information as reference of structuring.

The corpus for learning includes a large amount of text data according to the format (sentence model) of a remark of a radiological report. The sentence model shows the configuration of the remarks of the radiological report like image capture parameters→region→basic findings (feature—conclusive words)→diagnosis (diagnosis—conclusive words). In the corpus for learning, for example, classification item names of the elements constructing the sentence model of the remarks included in a model of a radiological report (also called "report model") are tagged to words and phrases.

Examples of the element classification items are "category of a diagnosis (hereinafter, called "category")", "image capture parameter", "region", "basic findings", "diagnosis", and the like.

In the corpus for learning, for example, the classification item name "category" of an element is tagged to each of phrases such as "brain infarction" and "ischemic change". The element classification item name "image capture parameter" is tagged to each of phrases such as "T1 image" and "T2 image". The element classification item name "region" is tagged to each of phrases such as "frontal lobe" and "temporal lobe". The element classification item name "basic findings" is tagged to each of phrases such as "dot-, spot-state high signal area" and "dot-state high signal area". The element classification item name "diagnosis" is tagged to each of phrases such as "old brain infarction" and "wide-ranged old brain infarction".

When such a corpus for learning is given from the outside to the data constructing unit 123, to create new report data with an image which will be described later, data showing a representative sentence model in which a conclusive word is specified to certain extent is also given from the outside.

The machine learning function of the data constructing unit 123 extracts words and phrases from the corpus for learning and stores them by a corresponding element classification item. Specifically, the data constructing unit 123 uses teaching data including the corpus for learning as learning materials, and learns and stores words and/or phrases belonging to each of the element classification items with reference to the teaching data. In this operation, data learned and stored is used as data of a model (model data) indicative of decomposition of the elements constructing an existing radiological report to element classification items.

Further, the identifying function of the data constructing unit 123 identifies an element classification item and an actually used words or phrases in the radiological report input to the data constructing unit 123 while using the model data learnt as described above as a reference. Accordingly, the data constructing unit 123 functions as a character information extracting unit.

By using the above-described machine learning method, the element classification items of only elements (in the embodiment, words and phrases) listed in the teaching data can be identified. However, by using the following machine learning method, the element classification items of also elements which are not preliminarily listed in the teaching data can be identified.

For example, the machine learning function of the data constructing unit 123 disassembles the corpus for learning into morphemes by a morphological analysis and learns, for each of morphemes, a pattern in which a morpheme belonging to a certain classification item appears by using information such as the morpheme itself, the word class of the morpheme, the inflected forms of the morpheme, and preceding and subsequent morphemes (for example, two preceding morphemes and two subsequent morphemes). The identification function of the data constructing unit 123 can recognize the element classification item of also an element (in this case, character information such as a word and a phrase) which has not been preliminarily given in accordance with the pattern.

More concretely, for example, in the case where a sentence such as "along" (various words can be used for the part "") frequently appears in the corpus for learning and words and phrases indicative of a region frequently appears in the part "", the machine learning function of the data constructing unit 123 can learn a pattern that words or phrases indicative of a region enters in the part "". By using such a pattern, the identifying function of the data constructing unit 123 can extract "hypophysis" as a word indicative of a region from the phrase "along/a/hypophysis" based on the context in an existing radiological report as an object. The machine learning can be realized by using so-called SVM (Support Vector Machine). By such machine learning, the precision of the natural language process improves.

In such a manner, the data constructing unit 123 extracts a plurality of pieces of character information constructing report data with an image by conducting the language analysis on the report data with an image included in the report DB 211.

The data structuring function of the data constructing unit 123 structures report data with an image by decomposing various information included in the report data with an image and attribute information into words and/or phrases (elements) belonging to the respective element classification items on the basis of information identified by the identifying function and describing the words and/or phrases in the RDF language.

Figure 6:
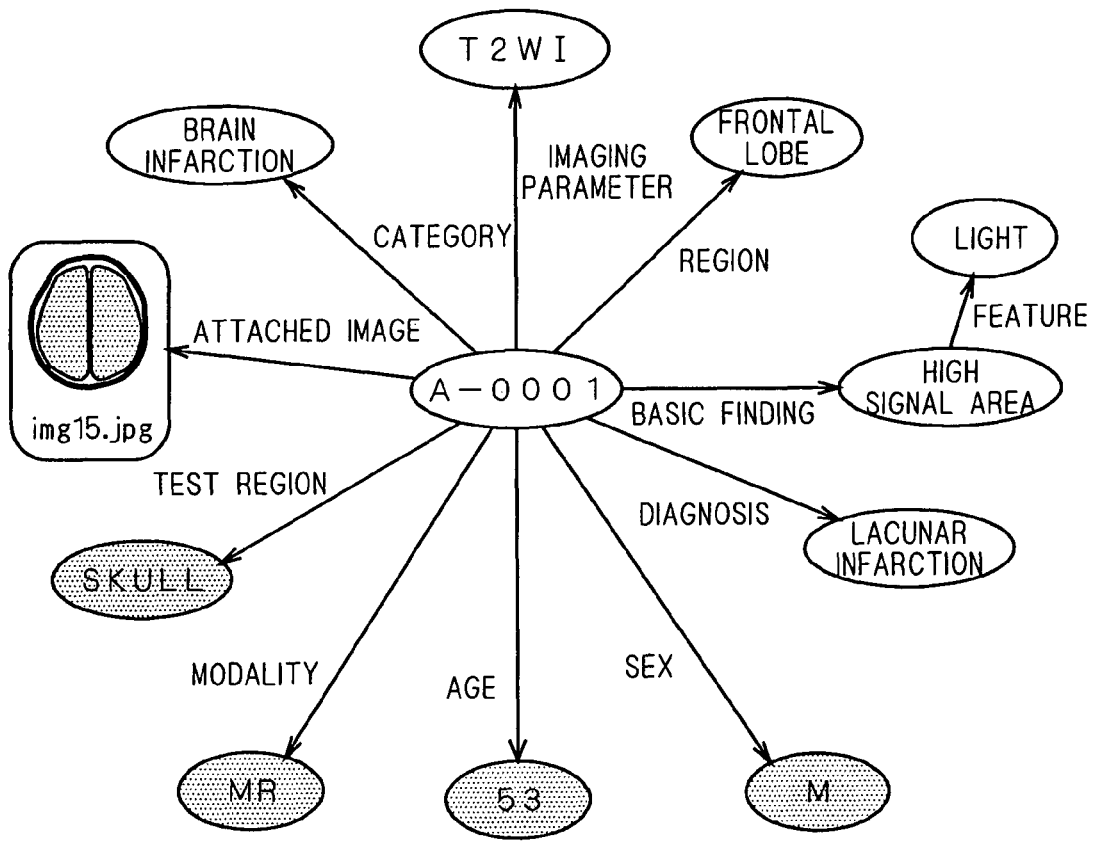
FIG. 6 is a diagram illustrating single report structured data.

FIG. 6 is a diagram illustrating data obtained by structuring elements of a single radiological report (also including elements constructing the attribute information of the existing radiological report). As shown in FIG. 6, for a file "A-0001" of report data with an image, attribute values "brain infraction", "T2WI", "frontal lobe", "high signal area", and "lacunar infarction" are described so as to be associated with, as attribute items, the element classification items "category", "image capture parameter", "region", "basic findings", and "diagnosis", respectively. For the attribute value "high signal area", when the element classification item "feature" is used as the item of an attribute, an attribute value "light" is described so as to be associated with the attribute.

In the file "A-0001" of the report data with an image, by the RDF, "attached image" and attribute items "test region", "modality", "age", and "sex" related to attribute information of image data are used as attribute items, and the file name "img15.jpg" of the image data, "skull", "MR", "53", and "male (M)" are associated as attribute values with the attribute items, respectively. The attribute items to be associated in the single report structured data are not limited to the eleven classification items shown in FIG. 6 but predetermined number of classification items including other attribute items included in, for example, information of test attributes and other items constructing a natural sentence such as "conclusive word" and the like. Although only one piece of image data is associated in FIG. 6, a plurality of pieces of image data may be associated.

In this case, the attribute values are directly associated with the file "A-0001" of the report data with an image, so that the image data is indirectly associated with the attribute values of the attribute items other than the attached image via the file name "A-0001". The invention is not limited to the arrangement. The image data and the attribute values of a part or all of the attribute items may be directly associated with each other. For example, the attribute values "skull", "MR", "53", and "male (M)" of the attribute items "test region", "modality", "age", and "sex" of the attribute information of the image data may be directly associated with the attribute value "img15.jpg" indicative of the file name of image data.

The data constructing unit 123 generates single report structured data as shown in FIG. 6 for each of a number of pieces of tested report data with images which are stored in the diagnosis information DB 210 by the machine learning function, the identifying function, and the data structuring function.

By storing, in the diagnosis information DB 210, a number of pieces of the single report structured data generated by associating a plurality of pieces of character information constructing report data with an image and one or more pieces of image data as an object to be interpreted in the report data with the image for each of a plurality of pieces of report data with images stored in the report DB 211, the association information DB, that is, the structured DB 213 corresponding to the retrieval support information for supporting the retrieving operation is constructed.

In the data constructing unit 123, a process of arranging a plurality of attribute values associated in each single report structured data by attribute items, re-associating the attribute values, and describing the attribute values in the RDF language is performed on all of a number of pieces of single report structured data. As a result of the process, a plurality of attribute values (in this case, character information such as words) are listed by attribute items included in a plurality of attribute items, and information in which the attribute values are associated with each other between the attribute items so as to form a network (network information) is created. By storing the network information in the storing unit 110, the information for supporting input of a new radiological report (input support information), that is, the input support DB 111 is constructed.

In this case, the structured DB 213 and the input support DB 111 can be easily described by using the RDF language.

Figure 7:
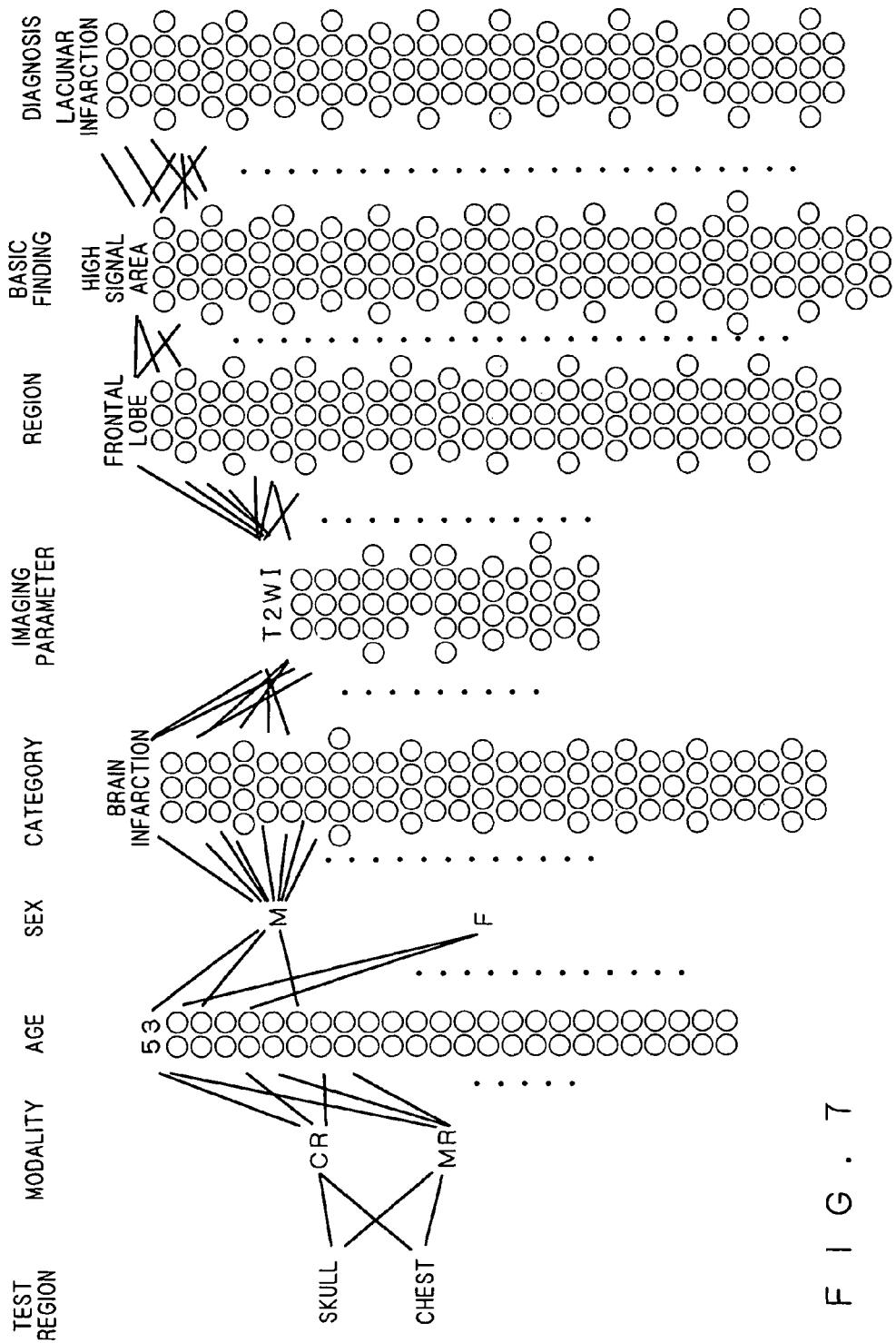
FIG. 7 is a diagram showing an example in which elements related to a number of existing radiological reports are structured.

FIG. 7 is a diagram showing an example in which elements of a number of existing report data with images are structured, and illustrates network information on the test regions "skull" and "chest". In FIG. 7, associated words and phrases are connected via solid lines. In FIG. 7, to avoid complication of the drawing, words and phrases are illustrated as "OOO" and the like and, as solid lines indicative of association, only lines which are positioned in an upper part in the diagram are illustrated and the other solid lines are not shown.

At the time of creating network information by the data constructing unit 123, the number of combinations of words and phrases among the associated items in every single report structured data is counted, and the counted information is stored in the input support DB 110. For example, the number of combinations of words and phrases such as "skull—MR—53—M—brain infarction—T2WI—frontal lobe—high signal area—lacunar infarction" is stored as count information.

In the network information stored in the input support DB 111, words and phrases in an existing radiological report are shown in a mode in which they are associated with each other between the attribute items. Consequently, it is effective to output the network information in a visible form and use it at the time of inputting a new radiological report. In particular, it is effective to provide the network information in the form of a template in which the attribute items are set as input element items and a plurality of words and phrases listed for the attribute items are set as input candidates (options).

However, in the network information stored in the input support DB 111, when there are too many synonyms (for example, "T2 emphasized image", "T2W1", and the like) for any of the words and phrases listed for the attribute items, options becomes too many, and it is difficult to designate an option. Consequently, at the time of detecting a word and/or a phrase, by the identifying function of the data constructing unit 123, a process of replacing synonyms with a single representative word and/or phrase is performed. In the case where "conclusive words" or the like exist in the attribute items, when there are too many expressions for conclusive words or the like (for example, "is considered" and "will be considered"), the number of options becomes too large, and it is difficult to designate an option. With respect to variations in expression, at the time of detecting conclusive words, by the identifying function of the data constructing unit 123, a process of replacing words to one representative expression is performed.

Such replacement of words or phrases to one representative word or phrase can be realized by including a table in which a plurality of words or phrases and a representative word or phrase are associated with each other in the teaching data. With respect to the variations in expression, the variations may be normalized and replaced with the expression used most frequently. Synonyms may be also replaced with a synonym used most frequently.

In a radiological report, for example, as the attribute item "basic finding", a phrase (basic finding phrase) in which rough classification and a modifier showing a feature are combined is often used. For example, the basic finding phrase "light high signal area" is combination of the rough classification "high signal area" and the feature "light".

As described above, the basic finding phrases (for example, "light high signal area", "dark high signal area", and the like) are constructed by a number of combinations of rough classification and the feature, so that the number of options is too large, and it is difficult to designate an option. Consequently, for example, with respect to the attribute item "basic finding", the element of the basic finding phrase is decomposed to two element items "rough classification" and "feature".

The process of decomposing the element into two element items is realized by using the known SVM or the like employing, as a reference, a model in which language elements belonging to the element items are listed. The model used here can be obtained by, for example, machine learning using teaching data including a corpus in which a number of basic finding phrases are listed. In the corpus, the item names of a number of language elements constructing a basic finding phrase are tagged.

Figure 8:
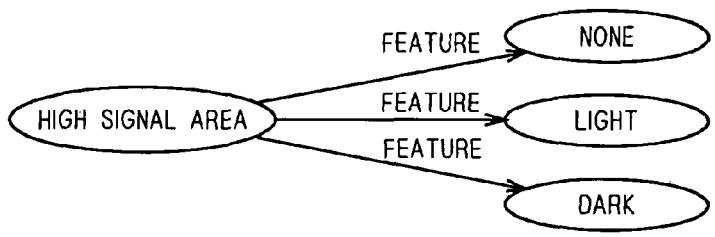
FIG. 8 is a diagram illustrating information obtained by associating detailed elements by description of RDF.

With respect to the attribute item "basic findings" in the network information, a basic finding phrase corresponding to a term of a rough classification is replaced with the term of the rough classification. Besides the network information, as shown in FIG. 8, information (detailed information) in which detailed elements such as features (modifiers) combined to form a basic finding phrase are associated with a term of the rough classification is generated by the RDF description. By the detailed information, structured data (detailed information structured data) in which an element with which the detailed element is associated (element with detailed information) and the detailed element are associated with each other is generated.

Concretely, in FIG. 8, the detailed elements "none", "light", and "dark" belonging to the item "feature" of the detailed element are associated with the term "high signal area" of the rough classification as an element with detailed information.

For example, a phrase belonging to a certain item such as the basic finding phrase also corresponds to detailed elements for a term of large classification corresponding to an element belonging to the item. Therefore, the following "detailed element" includes a detailed element as a component of a phrase such as a feature, and also a phrase as a result of combination of a plurality of detailed elements.

Since the network information, count information, and detailed information are information indicative of association of elements (in this case, words and phrases) belonging to a plurality of items among the items, it will be also called "element network information". The count information is information indicative of strength of association among a plurality of elements including one or more detailed elements (also called "association strength information")

Figure 9:
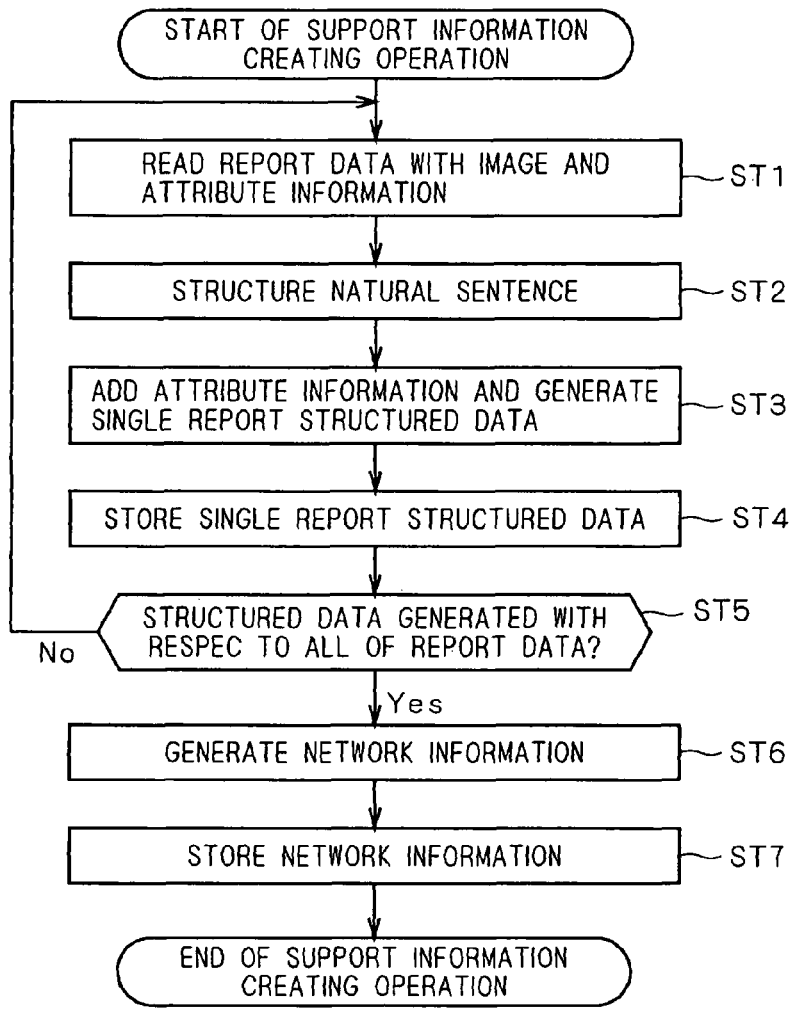
FIG. 9 is a flowchart showing the flow of support information creating operation.

FIG. 9 is a flowchart showing the flow of the support information creating operation. The operation flow is realized by executing the program for realizing the input support function in the control unit 120 in the server 100. As the discussion to follow regarding the flowchart will show, the control unit 120 functions as a storage controlling unit.

In step ST1, the data reading unit 121 and the test determining unit 122 read report data with an image together with attribute information from the diagnosis information DB 210.

In step ST2, a remark as a natural sentence expressed by the report data with an image is structured by the function of the data constructing unit 123.

In step ST3, by the data constructing unit 123, the attribute information is added to the data structured in step ST2. As a result, single report structured data as shown in FIG. 6 is created.

In step ST4, the single report structured data created in step ST3 is stored in the diagnosis information DB 210. By repeating the process of storing the single report structured data in step ST4, the structured DB 213 is constructed.

In step ST5, the data constructing unit 123 determines whether or not the single report structured data has been created with respect to all of the report data with images stored in the report DB 211. In the case where the single report structured data has not be created with respect to all of the report data with images, the program returns to step ST1. The next report data with an image is read together with attribute information, and single report structured data is generated and stored. In the case where the single report structured data is generated with respect to all of report data with images, the program advances to step ST6.

In step ST6, by the data constructing unit 123, network information as shown in FIG. 7 is generated on the basis of the single report structured data of all of the report data with images.

In step ST7, the network information generated in step ST6 is stored in the storing unit 110, thereby constructing the input support DB 111, and the operation flow is finished. The element network information including the network information and the count information is generated and stored in the input support DB 111.

The number of pieces of report data with an image stored in the diagnosis information DB 210 increases each time new report data with an image is created in accordance with an input from the report input device 30. It is effective when radiological reports being stored with time can be also used as past knowledge. In particular, in the case where new remarks are included in a newly stored radiological report, the past knowledge is further enriched, so that it is more effective. As will be described later, in response to designation of an actually input element for each of the items of elements constructing a remark of a radiological report in the input supporting operation (which will be described later), the knowledge in the past enriches.

Test Selecting Operation

Next, an operation of displaying a screen showing a test list (test list screen) and selecting a report input target test (test selecting operation) in the report input device 30 will be described.

The test selecting operation is realized by the input support function. The data reading unit 121 reads test list information from the diagnosis information DB 210 and transfers it to the control unit 31 in the report input device 30. The control unit 31 displays the test list screen on the display unit 33 on the basis of the test list information by the function of the display control unit 312.

FIG. 10 is a diagram illustrating a test list screen G1. As shown in FIG. 10, the test list screen G1 is a screen displaying a list of information of a test (concretely, patient ID, patient's name, birthday, age, sex, state, test ID, test date, test region, modality, and the number of images).

It is understood that, in the test list screen G1, a test whose state is "not read yet" is a test whose radiological report is not generated.

In the test list screen G1, a box cursor CS1 surrounding a test is displayed. The box cursor CS1 is moved vertically in response to an operation on the operating unit 32 of the user. When a determination button (for example, return key) in the operating unit 32 is depressed in a state where the box cursor CS1 is on a desired test, the test surrounded by the box cursor CS1 is selected as a report input target test. After the report input target test is selected in such a manner, the screen displayed on the display unit 33 changes from the test list image G1 to a radiological report input screen G2 (which will be described later).

In the test selecting operation, for example, when the report input target test is selected on the test list screen as shown in FIG. 10, combination of an element (for example, skull) belonging to the item "test region" and an element (for example, CR) belonging to the item "modality" is simultaneously designated and recognized.

When the report input target test is selected, the task managing unit 311 specifies a task to generate a new radiological report corresponding to the report input target test. At this time, under control of the task managing unit 311, the ordered matter corresponding to the report input target test and the attribute information indicating the details of the test in the diagnosis information DB 210 is read by the data reading unit 121 and provided for the control unit 31 in the report input device 30.

Input Supporting Operation

Next, the case of displaying a screen for inputting a new radiological report (radiological report input screen) and inputting a new radiological report in the report input device 30 will be described. Data of various screens displayed on the display unit 33 of the report input device 30 is input from the server 100, and the display control unit 312 in the report input device 30 realizes screen display in the display unit 33 on the basis of the input data.

Figure 11:
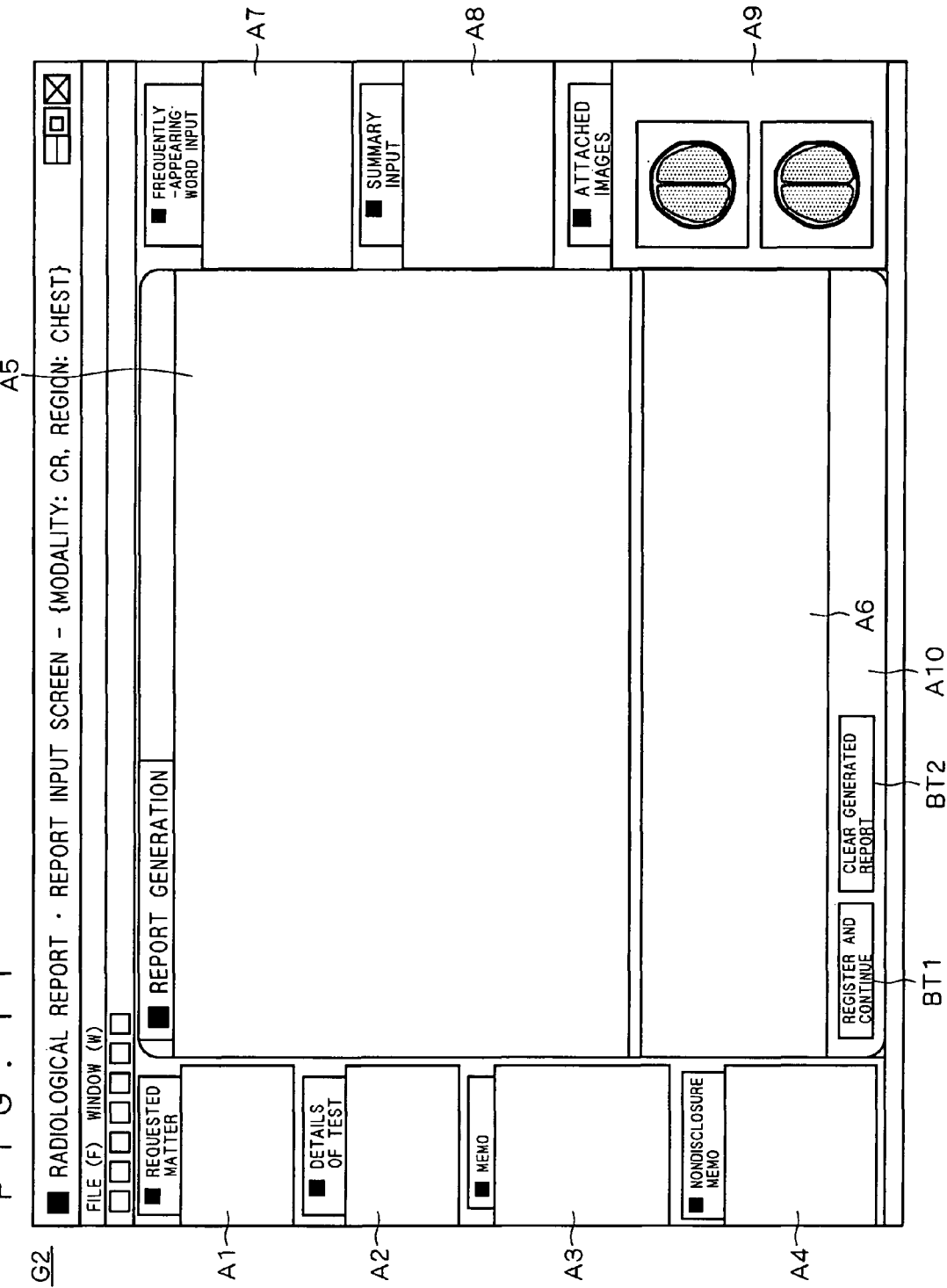
FIG. 11 is a diagram illustrating a radiological report input screen.

FIG. 11 is a diagram illustrating the radiological report input screen G2. As shown in FIG. 11, the radiological report input screen G2 is constructed by, mainly, a requested-matter display area A1, a test information display area A2, a memo area A3, a nondisclosure memo area A4, a generation support information display area A5, a remark display area A6, a frequently-appearing word display area A7, a summary display area A8, an image attachment area A9, and a command display area A10.

In the requested-matter display area A1, a requested matter related to a report input target test is displayed. Concretely, for example, a requested-matter as shown in FIG. 12 is displayed in the requested-matter display area A1 on the basis of information of a requested matter obtained from the diagnosis information DB 210 via the server 100.

In the test information display area A2, the details of the report input target test is displayed. Concretely, for example, the details of a test as shown in FIG. 13 are displayed in the test information display area A2 on the basis of information of the details of a test obtained from the diagnosis information DB 210 via the server 100.

In the memo area A3, a comment and other information is written freely according to an operation on the operating unit 32 of a reading physician.

In the nondisclosure memo area A4, like the memo area A3, a comment and other information is written freely according to an operation on the operating unit 32 of a reading physician. Information written in the nondisclosure memo area A4 can be viewed only by a specific device or a specific person.

For example, viewing can be limited by filtering using an IP address, entry of a password, or the like. Consequently, the nondisclosure memo area A4 can be used for managing personal information having high confidentiality.

The generation support information display area A5 is an area for visibly providing partial network information obtained (extracted) from the network information stored in the input support DB 111 to support generation of a radiological report. As will be described specifically later, in the generation support information display area A5, first, a screen for designating elements belonging to the item "category" is displayed. Network information according to an element belonging to the item "category" designated on the screen is obtained from the input support DB 111, and a screen visibly output in the form of a template (hereinafter, also called "input support template screen") is displayed. The input support template screen will be described specifically later.

In the remark display area A6, a remark constructing the radiological report is displayed. The remark is written in response to an operation on the operating unit 32 of a reading physician.

In the frequently-appearing word display area A7, a list of boilerplates (frequently-appearing words) which are frequently used in remarks is displayed. In the frequently-appearing word display area A7, for example, a list of frequently-appearing words as shown in FIG. 14 is displayed. By properly operating the mouse or the like of the operating unit 32, a reading physician can designate one of the frequently-appearing words in the list and copy (write) the frequently-appearing words designated in the cursor position in the remark display area A6.

In the summary display area A8, a list of boilerplates (summary) frequently used in remarks is displayed. For example, a list of boilerplates as shown in FIG. 15 is displayed in the summary display area A8. By properly operating the mouse or the like of the operating unit 32, a reading physician can designate one of the boilerplates in the list and copy (write) the boilerplate designated in the cursor position in the remark display area A6. Concretely, for example, when a boilerplate sentence "there is no finding" in the summary display area A8 is designated, the character string of "there is no finding" is copied in the remark display area A6.

It is sufficient to pre-store the information of a frequently-appearing word and a boilerplate sentence in the storing unit 110 or the like. For example, it is very convenient when one or more frequently-appearing words or boilerplates are stored in correspondence with a combination of elements belonging to the two items "test region" and "modality" and a list of the frequently-appearing words or boilerplates according to the combination of elements belonging to the two items "test region" and "modality" designated in the test list screen is displayed in the frequently-appearing word display area A7 or the summary display area A8.

In the image attachment area A9, a characteristic and representative image is attached. According to an operation on the operating unit 32 of the reading physician, a desired representative image is attached. For example, a mouse pointer is placed on a desired image in the images displayed in the left-half area LH of the image display screen 401 shown in FIG. 4. While pressing the left button of the mouse, the mouse pointer is moved (dragged) to the image attachment area A9, and the finger on the left button of the mouse is moved off. By the operation, a desired image can be attached to the image attachment area A9.

In the command display area A10, icons (in this case, buttons BT1 and BT2) for inputting a command are listed. Concretely, the button BT1 is used for entering a command to determine a remark or an attached image constructing a radiological report generated in the radiological report input screen G2, register new report data with an image in the diagnosis information DB 210, and move to generation of the next radiological report (that is, report data with an image). The button BT2 is a button for entering a command to clear a remark and an attached image constructing a radiological report generated in the radiological report input screen G2 and re-generate a radiological report.

Next, the operation of inputting a remark constructing a radiological report by using a template displayed in the generation support information display area A5 will be described.

In the generation support information display area A5, network information generated as described above is visibly output in the form of a template. By properly designating options of elements (in this case, character information such as words) in the template, inputting of a remark (that is, inputting of a new radiological report) is executed.

However, when all of network information (whole network information) is simply provided in the form of a template displaying a list of a plurality of elements listed for the attribute items as options as shown in FIG. 7, the number of options listed becomes too large, and it becomes difficult to select an option. In the database system 1 as an embodiment of the present invention, for example, elements of a part of the attribute items in the whole network information are determined by a reading physician as the user, thereby obtaining (extracting) partial network information from the whole network information and displaying the partial network information. As described above, in the template displaying a list of the partial network information, the number of options listed is limited to some extent, so that it becomes easier to select the options.

Further, for example, various terms indicative of features are added for the term "high signal area" of rough classification belonging to an item of the basic findings, thereby constructing various basic finding phrases. Consequently, there is a number of basic finding phrases of one term of rough classification belong to a classification item of the basic findings. When all of the number of basic finding phrases (for example, "light high signal area" and "dark high signal area") are displayed in a list, the number of options listed is large, and it is difficult to select an option.

To address such a problem, a method of simply providing a new classification item of a detailed element such as "feature" in the list display may be considered. However, in such a method, the number of items in the list becomes too large, and it is not easily see them. Further, since it is not necessary to enter a detailed element for the classification item of the detailed element, it is difficult to know the minimum necessary items to generate a report.

In the list display in the database system 1, first, with respect to a plurality of basic finding phrases related to a term of rough classification, the term of rough classification is shown as a representative. In response to a predetermined instruction, detailed information of the plurality of basic finding phrases of the term of rough classification is displayed. With such a configuration, detailed information can be simply input while making the outline of a sentence of a remark (the minimum necessary items) remain clear.

A method of obtaining the partial network information from the whole network information will be described.

FIG. 16 is a diagram illustrating a template TP1 (information obtaining condition determining template) for determining conditions for obtaining desired partial network information from the whole network information (hereinafter, also called "information obtaining conditions" or "extraction conditions").

As described above, when a test is selected by the test selecting operation, on the radiological report input screen G2 (for example, FIG. 11), for example, the requested matter (for example, FIG. 12) is displayed in the requested-matter display area A1, and the details (for example, FIG. 13) of the test in the report input target test is displayed in the test information display area A2. By the function of the information retrieving unit 125, the information obtaining condition determination template TP1 is displayed in the generation support information display area A5.

In the information obtaining condition determination template TP1, words and phrases (options) are listed for the attribute item "category" as one of the whole attribute items in the whole network information. The listed options of the attribute item "category" are, for example, elements of the item "category" associated with the combination of the elements belonging to the item "test region" and the elements belonging to the item "modality" designated simultaneously with selection of the report input target test in the test selecting operation.

For example, when the combination of the element "chest" belonging to the item "test region" and the element "CR" belonging to the item "modality" is designated in the test selecting operation, in the information obtaining condition determination template TP1, as shown in FIG. 16, the elements "lung", "soft part", "mediastinal space", "pleural membranes (marginal)", "bone", and "others" belonging to the item "category" are listed as options.

It is sufficient to pre-store the information of the options of the item "category" listed in the information obtaining condition determination template TP1 in the storing unit 110 or the like. For example, it is sufficient to store one or more elements of the item "category" in association with the combination of the elements belonging to the two items "test region" and "modality" and display, on the information obtaining condition determination template TP1, the list of options of the item "category" according to the combination of elements belonging to the two items "test region" and "modality" designated in the test list screen.

In the information obtaining condition determination template TP1, the reading physician variously operates the operating unit 32 to place a mouse pointer MP on a desired option and perform a predetermined operation (for example, double click), thereby designating an option belonging to the item "category".

In this case, the combination of the options determined in the test list screen (for example, FIG. 10 and the like) and the information obtaining condition determination template TP1 is designated as the information obtaining condition. For example, in the information obtaining condition determination template TP1 shown in FIG. 16, when the option "pleural membranes" belonging to the item "category" is designated, the combination of the element "chest" of the item "test region", the element "CR" of the item "modality" and the element "pleural membranes" of the item "category" is designated as the information obtaining condition. The information obtaining condition is supplied from the report input device 30 to the information retrieving unit 125 by the control unit 31.

The information retrieving unit 125 retrieves the input support DB 111 in accordance with a predetermined information obtaining rule in response to designation of the information obtaining condition from the report input device 30. From the whole network information, partial network information corresponding to the predetermined information obtaining rule and the information obtaining condition is obtained as information for displaying a list as a template in the generation support information display area A5 (hereinafter, also called "network information for display"). Concretely, partial network information narrowed to items specified in the predetermined information obtaining rule from the network information satisfying the information obtaining condition is obtained from the whole network information.

At this time, the information retrieving unit 125 can extract partial network information satisfying the information obtaining condition from the whole network information by referring to the count information stored in the input support DB 111. At this time, partial count information corresponding to the extracted partial network information is also extracted from the count information.

The partial network information and the partial count information will be also properly generically called "partial element network information". The partial network information and the partial count information will be properly simply called "network information" and "count information", respectively. When it is assumed that partial network information is extracted in the form described in the RDF language, the partial element network information and the network information after acquisition can be easily described.

A template is provided, visibly displaying a list of the partial network information extracted as described above. Since the provided template is to support input of a remark of a new radiological report, it will be also called "input support template" hereinafter.

Figure 17:
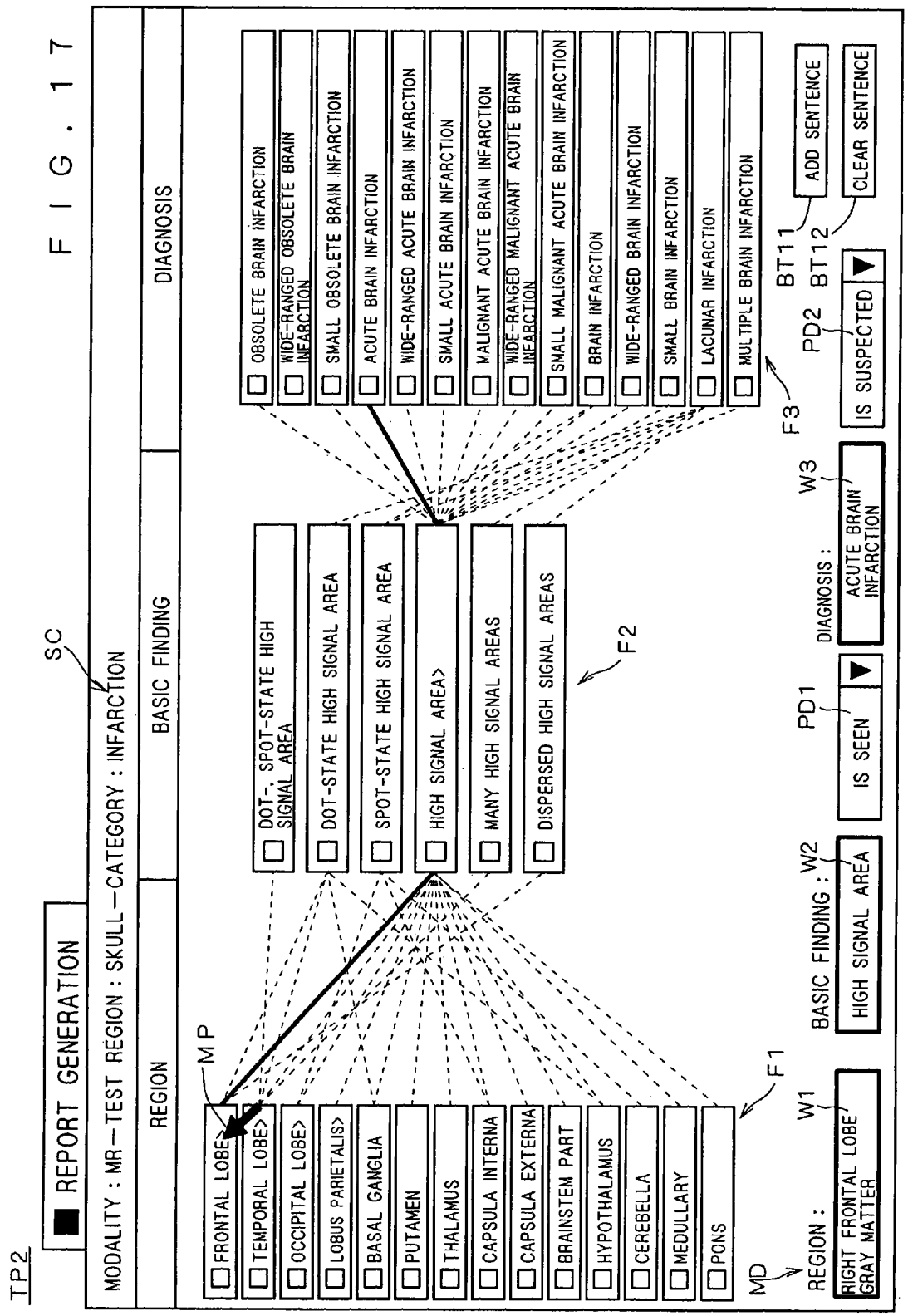
FIGS. 17 and 18 are diagrams showing an example of input support template display.

FIG. 17 is a diagram showing a display example of an input support template TP2. FIG. 17 shows the input support template TP2 which is displayed in the case where the combination of the element "MR" of the item "modality", the element "skull" of the item "test region", and the element "infarction" of the item "category" is designated as the information obtaining condition. Various inputs and designations in the input support template TP2 which will be described later are performed according to an input operation of the operating unit 32 by the reading physician.

As shown in FIG. 17, in the input support template TP2, information obtaining conditions SC are described at the top. A plurality of words and phrases F1, F2, and F3 in the items "region", "basic finding", and "diagnosis", respectively, are displayed in order from the left in a center area. Concretely, for the attribute item "region", a plurality of words and phrases ("frontal lobe>", and ... "pons") F1 are listed. For the attribute item "basic finding", a plurality of words and phrases ("dot-spot-state high signal area", ..., and "dispersed high signal areas") F2 are listed. For the attribute item "diagnosis", a plurality of words and phrases ("obsolete brain infarction", ..., and "multiple brain infarction") F3 are listed.

With respect to the three items "region", "basic finding", and "diagnosis", words and phrases associated with each other between the items are connected to each other via lines (in this case, broken lines) on the basis of the partial network information which is extracted under the information obtaining conditions. In such a manner, the partial network information narrowed to some extent is visibly displayed in a list.

Figure 18:
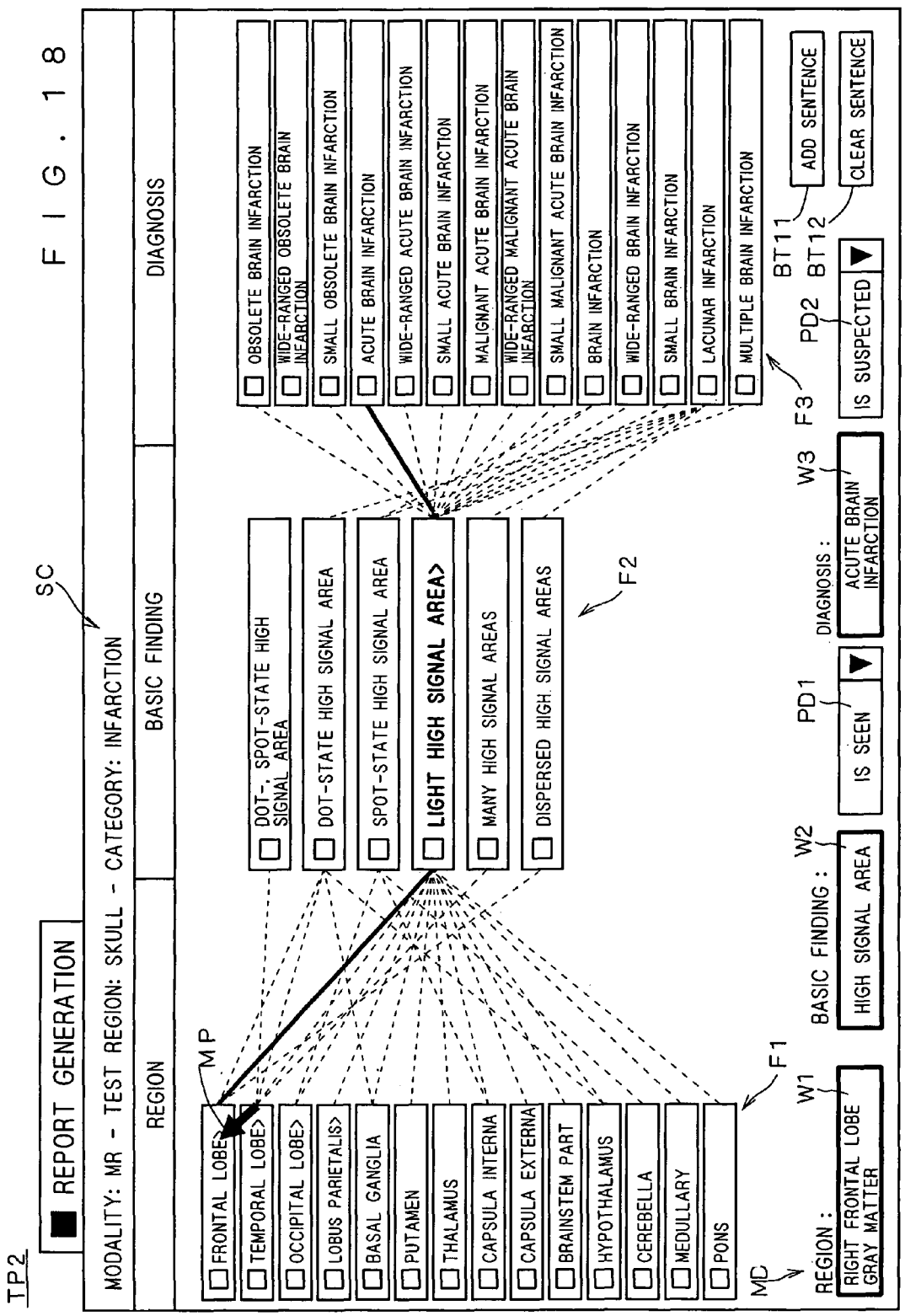

In FIG. 17, a word and a phrase with ">" such as the phrase "high signal area>" indicates a term of rough classification representing a plurality of basic finding phrases and region phrases. In the input support template TP2, when the mouse pointer MP is adjusted on a word or a phrase with ">" and right-clicking is performed, a popup list appears. When a desired phrase is selected by designating a proper detailed element, the selected desired phrase is filled in a blank (blank W1, W2, or the like) corresponding to the phrase. It is also possible to display a phrase of high use frequency in a popup list which appears when the mouse pointer MP is adjusted on a word or a phrase with ">" and the right button of the mouse is depressed, and to adjust the mouse pointer MP on the phrase, thereby enabling a phrase of high use frequency to be easily selected. When a desired phrase is selected by properly designating a detailed element, the term of rough classification may be replaced with the selected desired phrase (in this case, "light high signal area>") in the input support template TP2, as shown in FIG. 18.

At the time of designating a word and a phrase corresponding to each item, a sentence model MD of remarks in a radiological report, which is displayed in a lower part of the input support template TP2 is referred to by the reading physician. The sentence model MD is displayed on the basis of data of a report model (in this case, sentence model) supplied from the outside together with teaching data and the like.

The sentence model MD is a sentence model of remarks of a radiological report such as "region—basic finding—conclusive word. diagnosis—conclusive word". Concretely, a sentence model is shown such that "in [blank W1] [blank W2] [pull-down list PD1]. [blank W3][pull-down list PD2]". In the blanks W1 to W3, words for the items "region", "basic finding", and "diagnosis" are filled, respectively. In the pull-down lists PD1 and PD2, a conclusive word of the basic finding and a conclusive word of diagnosis are filled, respectively.

To be specific, by designation of words and phrases of a reading physician, one or more desired words and phrases (for example, "right front lobe gray matter") out of a plurality of words and phrases (options) F1 is filled in the blank W1. One word or one phrase (for example, "high signal area") out of a plurality of words and phrases (options) F2 is filled in the blank W2. One word or one phrase (for example, "acute brain infarction") out of a plurality of words and phrases (options) F3 is filled in the blank W3. The order of designation of words and phrases for the three items is not limited.

In the sentence model MD, with respect to conclusive words of a natural sentence along a predetermined sentence model other than the three items, a desired option can be designated by properly placing the mouse pointer MP on the pull-down lists PD1 and PD2. In FIG. 18, the conclusive words "is seen" are designated for the basic finding. The conclusive words "is suspected" are designated for diagnosis. The number of options for conclusive words may be three or more. The other words constructing a natural sentence such as adjective and adverb may be also selectively designated.

When the reading physician variously operates the operating unit 32 to adjust the mouse pointer MP on a button BT11 instructing "addition of sentence" and performs a predetermined operation (for example, left click) in a state where the words (properly including phrases) are designated for the three items and the two conclusive words, the words and phrases designated for the items and the like are determined as elements constructing a report along a predetermined report model by the control unit 31. Remarks of the radiological report displayed in the sentence model MD are copied to the remark display area A6.

On the other hand, when the mouse pointer MP is adjusted on a button BT12 instructing "clear of sentence" and a predetermined operation (for example, left click) is performed, all of the elements displayed in the sentence model MD, are cleared.

When a new remark is written in the remark display area A6 by using the input support template TP2 shown in FIG. 18 or the like, the mouse pointer MP is adjusted on the bottom BT1 at the bottom of the radiological report input screen G2, and a predetermined operation (for example, left click) is performed, an instruction of registering the new radiological report is given. To the report constructing unit 127, the elements constructing a new radiological report including the remarks displayed in the remark display area A6 and information indicative of the location of the image data attached to the image attachment area A9 are supplied. Since the elements constructing the remarks of the radiological report displayed in the sentence model MD (report elements) are designated for the corresponding items respectively, a new radiological report is input, for example, in the form of the single report structured data shown in FIG. 6.

In the report constructing unit 127, new report data with an image according to a predetermined rule is generated on the basis of the new single report structured data and the like and is added to the report DB 211 via the data writing unit 128. At this time, the new single report structured data is added to the structured DB 213. On the other hand, since the new single report structured data is added to the input support DB 111 by the data constructing unit 123, the input support DB 111 is updated.

Retrieving Operation

As described above, remarks can be easily entered in the input support template TP2. Although elements can be easily selected for some of the items constructing a remark at the time of inputting a remark, in a scene where the user cannot easily make determination in interpretation of radiogram due to lack of knowledge, it is difficult to select elements for the remaining items. In such a case, if the user can refer to an image similar to the image to be interpreted, included in the past case and remarks made on the similar image, it helps determination, and entry is facilitated.

The retrieving operation of retrieving and presenting an image similar to an image to be interpreted and a remark made on the similar image will be described below.

Figure 19:
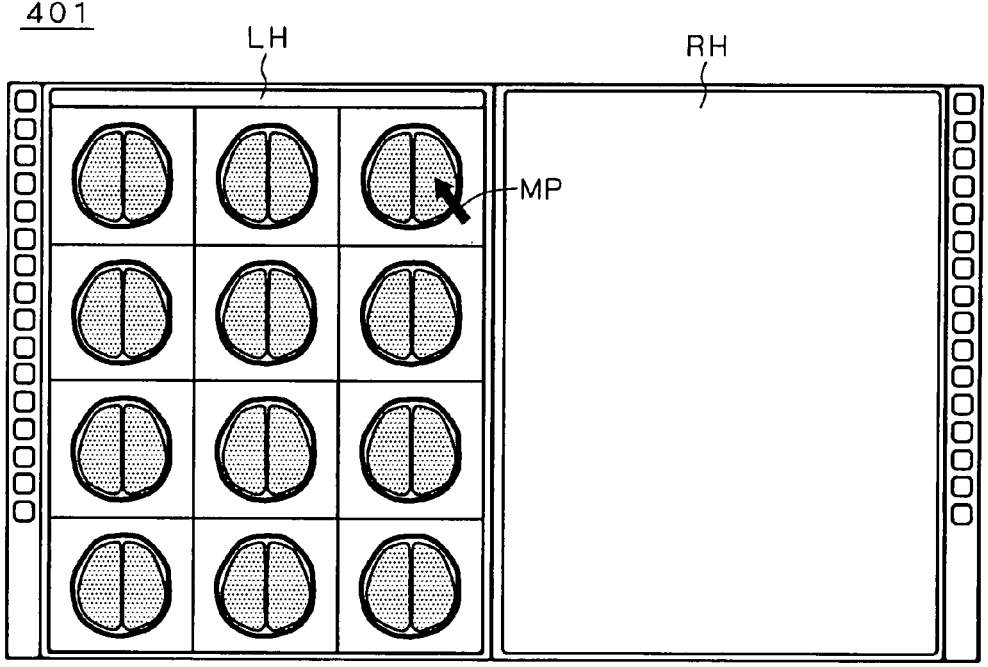
FIG. 19 is a diagram showing a display example of an image display screen.

FIG. 19 is a diagram showing an example of the image display screen 401 displayed on the report input device 30.

As shown in FIG. 19, at the time of inputting remarks, image data to be interpreted is visibly output in the left-half area LH in the image display screen 401. FIG. 19 shows a state where images of 12 pieces of image data are displayed.

Figure 20:
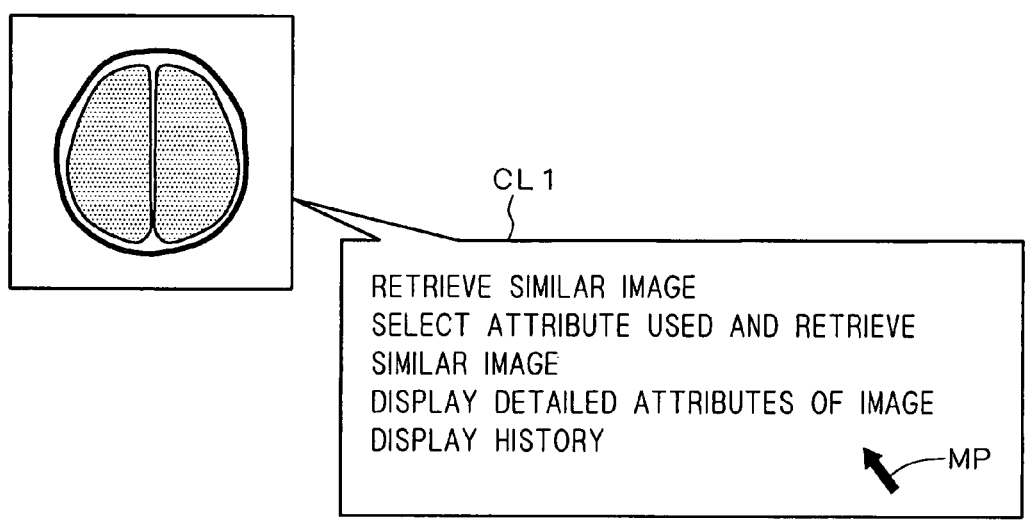
FIG. 20 is a diagram showing a list of commands related to retrieval.

When the reading physician variously operates the mouse included in the operating unit 32 to adjust the mouse pointer MP in a proper position in a plurality of images displayed in the area LH and clicks the right button of the mouse, a command list CL1 as shown in FIG. 20 appears. FIG. 20 shows the command list CL1 displayed on an image on which the mouse pointer MP is adjusted.

The command list CL1 includes a plurality of commands including four commands of "retrieval of similar image", "selection of attributes used and retrieval of similar image", "display of the detailed attribute of image", and "display of history". The reading physician adjusts the mouse pointer MP on a desired command by variously operating the image designating unit that includes the operating unit 32 and a mouse included with the operating unit 32. The operating of the image designating unit in this instance involves operating the mouse included in the operating unit 32 and clicks the left button of the mouse, thereby enabling the desired command to be designated.

First, the case of designating the command "retrieval of similar image" out of the plurality of commands in the list CL1 will be described.

In a state where an element (in this case, character information) of a part of a plurality of (five, in this case) classification items "region", "basic finding", "conclusive word", "diagnosis", and "conclusive word" of elements constructing a remark is designated in the input support template TP2, when "retrieval of similar image" is designated by the image designating unit, one or more images displayed in the area LH are designated as images as reference of retrieval (hereinafter, also called "retrieval reference image(s)"). That is, data of the retrieval reference image (retrieval reference image data) is designated.

When the retrieval reference image is designated by the image designating unit, in the input support template T2, the character information already designated with respect to part of the classification item is regarded as character information indicative of a feature of the retrieval reference image associated with the retrieval reference image (also called "character information for the image feature"). The character information for the image feature properly also includes character information constructing a DICOM attribute of the retrieval reference image and the attribute value of the information obtaining condition SC.

FIG. 21 is a diagram showing character information for image features.

In FIG. 21, character information is not designated for the attribute item "diagnosis". The attribute items Pf1 to Pf8 (in this case, character information "age", "sex", "modality", "test region", "imaging parameter", "region", "basic finding", and "feature") are associated with attribute values Pv1 to Pv8 (in this case, character information "53", "male", "MR", "skull", "T2WI", "frontal lobe", "high signal area", and "light"), respectively.

After the retrieval reference image is designated, a query of requesting retrieval of an image similar to the retrieval reference image using, as a retrieval keyword group, a plurality of pieces of character information constructing the character information for image features is transmitted from the control unit 31 to an image detecting unit, such as the information retrieving unit 125. The words "search keyword group" are used as concept including not only two or more character information but also single character information.

In response to reception of the query from the control unit 31, the information retrieving unit 125 detects one or more pieces of single report structured data to which an attribute value similar to the character information for image features is given with respect to predetermined classification items by a keyword search using text information on the structured DB 213 in the diagnosis information DB 210. As described below, herein and throughout the information retrieving unit 125 functions as an item designating unit.

The "predetermined classification items" are preliminarily set predetermined classification items as a part of a predetermined number of classification items to be associated in the single report structured data. Examples of the predetermined classification items are the classification items Pf3 to Pf7 shown in FIG. 21, that is, the five classification items "modality", "test region", "imaging parameter", "region", and "basic finding".

As described above, in the keyword search in the information retrieving unit 125, one or more pieces of character information belonging to the preset predetermined classification items as a part of the predetermined number of classification items to be associated in the single report structured data out of the plurality of pieces of character information associated with one or more retrieval reference image data (retrieval reference image) is selectively employed as a search keyword group. In such a manner, by selectively using the character information belonging to part of the items out of the character information added to the image data, the load on the keyword search process is reduced.

In the keyword search in the information retrieving unit 125, to prevent a failure in the search, one or more pieces of character information (hereinafter, also called "related character information") having a predetermined relation (such as synonym, near-synonym, related word, and the like) with one or more pieces of character information included in the search keyword group is extracted by referring to the dictionary DB 130. After the extracted character information is added to the search keyword group, keyword search is conducted. FIG. 22. is a diagram showing an example of data stored in the dictionary DB and shows a combination of "obsolete brain infarction" and "old brain infarction" and a combination of "T2WI", "T2WI-weighted image", and "T2WI image" having the relation of synonyms.

Since the single report structured data includes information indicative of the location of image data and the file name of report data with images, when one or more pieces of single report structured data are detected by the information retrieving unit 125, one or more pieces of image data and one or more pieces of report data with images are unconditionally detected. At this time, the image data detected by the information retrieving unit 125 has an attribute value similar to that given to the retrieval reference image data, so that the image data is detected as image data different from the retrieval reference image data and indicative of an image similar to the retrieval reference image data. Since the report data with images detected by the information retrieving unit 125 denotes the radiological report of the image similar to the retrieval reference image, data of the radiological report of the report data with images is detected as data of a report related to the retrieval reference image data (that is, related report).

As a result, the retrieval result display screen on which the similar image and the data of the related report detected as described above are visibly output is provided.

FIG. 23 is a diagram showing the details of display on the retrieval result display screen. The retrieval result display screen is displayed in the right-half display area RH of the image display screen 401.

In the retrieval result display screen shown in FIG. 23, two combinations of similar images, attribute information, and remarks of the report data with images are shown in order from the top. Concretely, similar images of the first report data with images are shown as similar images 1. Two images attached to the report data, attribute information (48 years old, female, skull, and MR), and remarks (high signal area is seen in the frontal lobe and occipital lobe in the T2WI-weighted image. Old brain infarction is suspected.) are displayed. Below the similar images 1, similar images of the second report data with images are shown as similar images 2. Two images attached to the report data, attribute information (68 years old, male, skull, and MR), and remarks (light high signal area is seen in the frontal lobe and the right temporal lobe in T2WI. Detailed test with CT is required.) are displayed.

With reference to the retrieval result display screen as shown in FIG. 23, the reading physician can easily designate proper character information for the classification item "diagnosis" and the like, to which designation of character information was difficult, on the basis of the remarks in the past by comparing the image to be interpretation with the similar images.

Next, the case of designating a command of "selection of attributes used and retrieval of similar image" from the plurality of commands in the list CL1 will be described.

In the case where the command "selection of attributes used and retrieval of similar image" in the list CL1 is designated, a setting screen for customizing search parameters as shown in FIG. 24 is displayed in the right-half display area RH of the image display screen 401.

In the setting screen shown in FIG. 24, the predetermined number (nine) of classification items to be associated in the single report structured data, "age", "sex", "modality", "test region", "imaging parameter", "region", "basic finding", "feature", and "diagnosis" are listed. A check box is provided on the left side of each of the classification items. In the setting screen, the reading physician as the user variously operates the mouse in the operating unit 32 to adjust the mouse pointer MP on a desired check box, and clicks the left button of the mouse, thereby making the check box provided on the left side of the classification item to be used for search a solid check box. By clicking the determination button with the mouse pointer MP, the keyword search with the customized search parameters can be executed.

With respect to the age, if similar images and related reports of patients of the same age as that of a patient of the retrieval reference image are retrieved, the amount of information obtained as a search result may be very small or unbalanced information may be obtained. Consequently, in the setting screen of FIG. 24, a certain range of ages can be set.

For example, in the setting screen of FIG. 24, five classification items "modality", "test region", "imaging parameter", "region", and "basic finding" are designated as classification items to be used for a search.

When there is not classification item to be used for a search, a keyword search cannot be executed. Therefore, in the setting screen, if at least one classification item out of the predetermined number of classification items is not set, even when the determination button is clicked, the keyword search is not executed.

In the keyword search in the information retrieving unit 125, one or more pieces of character information belonging to a part of the classification items set on the setting screen (FIG. 24) out of the predetermined number of classification items to be associated in the single report structured data in a plurality of pieces of character information associated with one or more pieces of retrieval reference image data is/are selectively employed as a search keyword group. As described above, by conducting a keyword search selectively using character information belonging to a desired classification item in the character information added to the retrieval reference image data, for example, a search can be performed by properly excluding items of character information which is not yet entered by the reading physician.

Figure 25:
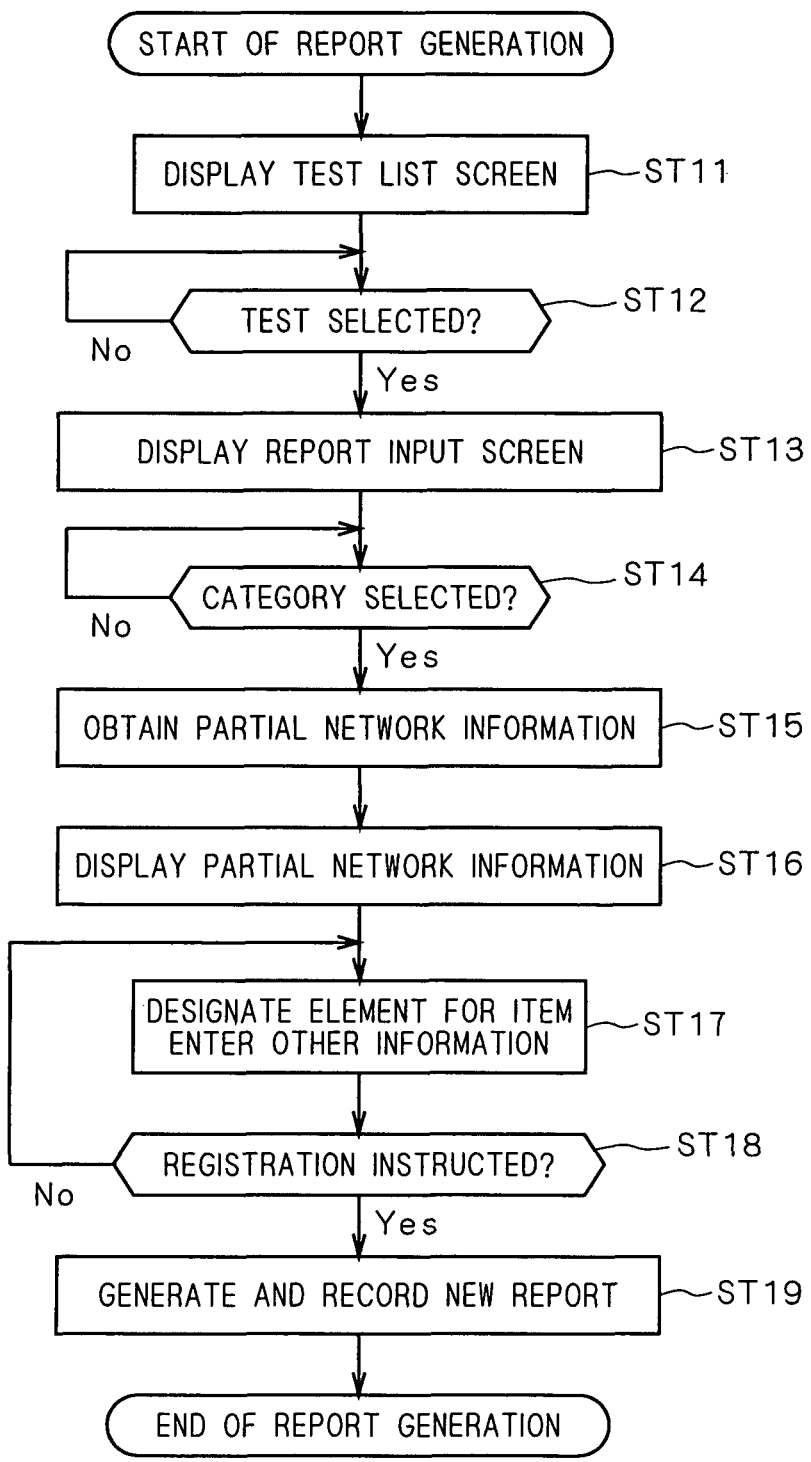
FIG. 25 is a flowchart showing a new report generating operation flow.

FIG. 25 is a flowchart showing a new report generating operation flow. When the report input device 30 performs a predetermined operation, first, the test selecting operation starts, and the program advances to step ST11 in FIG. 25.

In step ST11, a test list screen (for example, the test list screen G1 in FIG. 10) is displayed on the display unit 33.

In step ST12, whether a test on which a new radiological report is to be generated (report input target test) is selected on the test list screen or not is determined. The determination in step ST12 is repeated until the report input target test is selected. When the report input target test is selected, the program advances to step ST13.

In step ST13, the radiological report input screen G2 is displayed. In the generation support information display area A5 in the radiological report input screen G2, a screen (for example, the information obtaining condition determination template TP1 in FIG. 16) is displayed in which the elements (in this case, character information) belonging to the item "category" corresponding to the combination of the elements of the items "test region" and "modality" of the already selected report input target test are listed.

In step ST14, whether the character information of the item "category" is selected on the information obtaining condition determination template TP1 or not is determined. In this case, the determination in step ST14 is repeated until the character information of the item "category" is selected. After the character information of the item "category" is selected, the program advances to step ST15. By selecting the character information of the item "category", the information obtaining conditions are determined.

In step ST15, in response to input of the information obtaining conditions, partial network information is obtained from the whole network information stored in the input support DB 111. At this time, a part of the count information is also obtained.

In step ST16, the input support template TP2 to which the partial network information obtained in step ST15 is visibly output is displayed on the display unit 33.

In step ST17, an element is designated for each of the items in the input support template TP2, and the other information is entered. When the mouse pointer MP is adjusted on the button BT11 instructing "addition of sentence" and a predetermined operation is performed in a state where the character information (properly including phrases) is designated for each of the items and conclusive words by an input operation input of the reading physician operating the operating unit 32, remarks of the radiological report displayed in the sentence model MD are copied to the remark display area A6.

In step ST18, whether an instruction of registering the new radiological report is given or not is determined. In this case, the processes of steps ST17 and ST18 are repeated until the instruction of registering the new radiological report is given. When the mouse pointer MP is adjusted on the bottom BT1 at the bottom of the radiological report input screen G2 and the predetermined operation (for example, left click) is performed, the program advances to step ST19.

In step ST19, a new radiological report is constructed by the report constructing unit 127, and new report data with images is recorded to the diagnosis information DB 210 by the data writing unit 128. At this time, the new single report structured data entered to the input support template TP2 is added to the structured DB 213. By the function of the report constructing unit 127 and the data constructing unit 123, the new single report structured data is also used as data for reinforcing information stored in the input support DB 111. Specifically, each time new single report structured data is entered, while the data is added to the whole network information stored in the input support DB 111, the count information is also updated.

Figure 26:
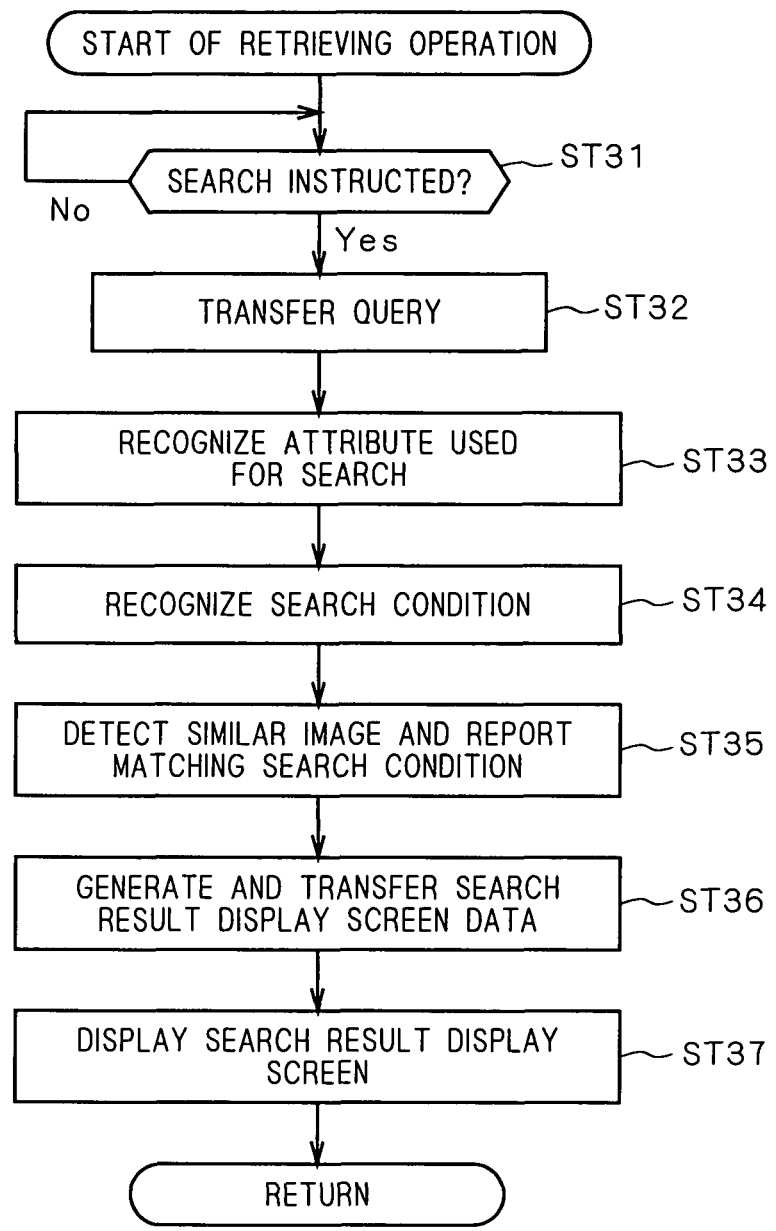
FIG. 26 is a flowchart showing a similar image/relation report retrieving operation flow.

FIG. 26 is a flowchart showing the operation flow of retrieving a similar image and a related report. The operation flow starts when the program advances to step ST16 in FIG. 25, and the program advances to step ST31 in FIG. 26.

In step ST31, by the control unit 31, whether the retrieval reference image data is designated by an operation on the operating unit 32 of the reading physician and an instruction of conducting a keyword search (search instruction) is give or not is determined. A search instruction is given when "retrieval of similar image" is designated in the command list CL1 as shown in FIG. 20 or the search parameters are customized in the setting screen as shown in FIG. 24 after "selection of attributes used and retrieval of similar image" is designated in the list CL1. Until the search instruction is given, the process of step ST31 is repeated. After the search instruction is given, the program advances to step ST32.

In step ST32, a query of requesting retrieval of an image similar to the retrieval reference image and a related report is transferred from the control unit 31 to the information retrieving unit 125. When the search parameters are customized, information of the customized search parameters is also transferred to the information retrieving unit 125.

In step ST33, at least one attribute, that is, at least one classification item used for the keyword search which are preset or customized are recognized by the information retrieving unit 125.

In step ST34, the search parameters are recognized by the information retrieving unit 125. Concretely, the character information belonging to the classification item recognized in step ST33 in the attribute values (in this case, character information) associated with the retrieval reference image is recognized as a search keyword.

In step ST35, the data of a similar image and a related report matching the search parameters recognized in step ST34 is detected by the keyword search by the information retrieving unit 125.

In step ST36, by the information retrieving unit 125, search result display screen data of the search result is generated on the basis of the data of the similar image and the related report detected in step ST35 and transferred to the control unit 31. Thus, the information retrieving unit 125 functions as a transmitting unit during the transfer of the search result.

In step ST37, by the control of the display control unit 312, the search result display screen is displayed on the display unit 33 on the basis of the search result display screen data generated in step ST36. That is, one or more pieces of image data and one or more pieces of report data detected in step ST35 are visibly output.

As described above, in the database system 1 of the embodiment of the invention, character information constructing a report (in this case, a radiological report) in which detailed information of image data is written is added as metadata to the image data. For example, only by designating an image being interpreted as an image used as a reference of retrieval (retrieval reference image) during interpretation of radiogram by a reading physician as the user, the character information already added to the retrieval reference image is used as a keyword, and data of a similar image and a related report with respect to the retrieval reference image data is detected by the keyword search using the metadata. By using, as metadata, the character information constructing a report of detailed features of an image and only by designating the image, the search parameters are determined. Thus, image retrieving precision is high and the search parameters can be easily entered.

In particular, since the radiological report is often associated with images and formed as a database, and the radiological report includes a large amount of character information expressing detailed features of the image, the metadata can be easily added to the image data and the retrieval precision can be easily improved.

Since the character information constructing the report data with images originally associated with image data is automatically added as metadata to the image data, a special operation of adding metadata to an image is unnecessary. Therefore, metadata can be easily added to an image.

Further, the character information added as metadata to image data is character information indicative of features of an image such as an imaging parameter, a region, a basic finding, a feature, diagnosis, a conclusive word, and the like. Therefore, the retrieval precision can be improved.

By also including attribute information of a DICOM attribute or the like originally added to image data into the metadata, the retrieval precision can be further improved. For example, by including attribute information of items featuring an image (for example, the patient ID, age, sex, modality, test region, primary doctor, and the like) into the metadata, a search using the character information of the items featuring the image can be realized. Thus, the retrieval precision can be further improved.

A keyword search also using a keyword having a predetermined relation (for example, the relation of synonym, a related word, and the like) with a keyword given first is conducted using the dictionary DB 130. Consequently, the probability of detecting data of a desired similar image and a desired related report increases irrespective of preference of words slightly varying among persons who generate radiological reports.

Modifications

Although the embodiment of the present invention has been described above, the invention is not limited to the above description.

For example, in the foregoing embodiment, both of a similar image and a related report are detected. The invention is not limited to the case. At least one of a similar image and a related report may be detected and presented to the user.

Also, in the foregoing embodiment, at the time of generating a new radiological report, a characteristic and representative image out of a plurality of images displayed in the display area LH is attached to the image attachment area A9 in the input support template TP2. The invention, however, is not limited to the embodiment. For example, in the case where a characteristic and representative image is not attached to the image attachment area A9, report data with an image in which a group of images displayed in the display area. LH is associated with the radiological report is generated. In such a case, in the single report structured data shown in FIG. 6, for example, it is sufficient to make the folder name indicative of the location of the group of images associated. In the case where the report data with images associated with the group of images is detected by a keyword search, all of the images in the group of images are displayed as a group of similar images on the search result display screen.

Although the data of a similar image and a related report of image data to be interpreted are retrieved in the foregoing embodiment, the invention is not limited to the retrieval. For example, the data of a similar image and a related report of image data indicative of the state with time of a patient to be interpreted may be retrieved. An example of the configuration will be described below.

For example, when a command "display of history" in the list CL1 shown in FIG. 20 is designated, a screen showing information of report data with images indicative of the past state of a patient to be interpreted (history display screen) as shown in FIG. 27 is displayed in the display area RH. In FIG. 27, information including images, attribute information, and remarks of the report data with images of last time is displayed as a related image 1. Information including images, attribute information, and remarks of the report data with images of last time but one is displayed as a related image 2.

By adjusting the mouse pointer on a desired image and clicking the right button of the mouse on the history display screen shown in FIG. 27 like in FIG. 20, a command list is shown. The command "retrieval of similar image" or "selection of attribute used and retrieval of similar image" in the list is designated and an operation similar to that of the foregoing embodiment is performed, thereby detecting a similar image or related report of the image displayed on the history display screen and presenting it by the report input device 30. With such a configuration, a related image already tested is designated as the retrieval reference image, and one or more pieces of character information directly and/or indirectly associated with the image data of the retrieval reference image in the structured DB 213 is/are designated as a search keyword group.

For example, in the case where a radiological report of a certain image to be interpreted is hardly input at present, the amount of character information associated with the image data to be interpreted is small. Therefore, when the data of a similar image and a related report of the image data to be interpreted are directly retrieved, the amount of character information included in the search keyword group is too small, and the precision of the keyword search deteriorates. Consequently, by employing a configuration of detecting data of a similar image and a related report of image data indicative of the state in the past in which a radiological report was already generated, that is, the configuration of indirectly retrieving data of a similar image and a related report of image data to be interpreted, the precision of the keyword search can be improved. Since a remarkable change is not generally seen between an image showing a past state and an image to be interpreted at present, the configuration is effective to improve precision of the keyword search.

Although the data of a similar image and a related report of the image data to be interpreted are directly or indirectly retrieved in the foregoing embodiment, the invention is not limited to the embodiment. For example, another configuration having a retrieving function may be employed, in which an image already tested (that is, its radiological report has been generated) is designated as the retrieval reference image, the data of a similar image and a related report of the retrieve reference image is detected from a number of pieces of single report structured data to be retrieved, which is included in the structured DB 213, and the detected similar image and related report is presented to the report input device 30. In such a configuration, when an image already tested is designated as a retrieval reference image, one or more pieces of character information directly and/or indirectly associated with image data of the retrieval reference image in the structured DB 213 is/are designated as a search keyword group.

By employing such a configuration, a number of images similar to an image of each case are collected and a representative image can be selected from each of the cases. Therefore, a teaching file can be generated easily.

The teaching file is provided to file representative cases and characteristic cases, so that doctors can easily refer to the cases. Once the teaching file is generated, it is very useful for training of doctors, diagnosis, and the like. However, it takes long time and high cost to generate the file. After a file is generated, various maintenances are necessary.

In this case, generation of a teaching file is facilitated and, moreover, a number of reports related to images of the cases can be collected so that the teaching file can be easily enriched. The configuration is effective also at the time of maintenance such as updating of the teaching file.

The configuration can be effectively used also in a training mode as described below.

For example, at the time of medical training, image data as a good example is given. When character information indicative of the details of the image data is associated with the image data, by using the retrieving function, other image data of cases similar to that of the example can be retrieved. Therefore, a trainee conducts diagnosis with reference to images of the image data as a good example and retrieves and refers to a similar image and a related report of the image data as a good example, so that the user can compare a diagnosis result of the user with a general diagnosis result. After that, the user can also retrieve the data of images and reports showing how the condition changes.

In the foregoing embodiment, words having the relation of synonyms, related words, and the like are stored so as to be associated in the dictionary DB 130. The invention is not limited to the embodiment. For example, words and phrases having the same meaning may be stored so as to be associated with each other, words and phrases having similar meaning may be stored so as to be associated with each other, and words and phrases having related meaning may be stored so as to be associated with each other. That is, in a keyword search, so-called ontology that follows up various relations may be used.

Further, the dictionary DB 130 may include a database in which the hierarchical relations in concept of character information are organized such as thesaurus in which various terms are organized hierarchically. A retrieving operation in the case where a thesaurus 19 in which words are organized hierarchically or the dictionary DB 130 includes the thesaurus will be described below.

FIG. 28 is a diagram showing the hierarchical structure of the thesaurus 19. As shown in FIG. 28, the highest layer in the hierarchical structure of the thesaurus 19 is roughly classified. From each of the rough classifications, words included in the first, second, and third layers are branched. In the thesaurus 19, the words are systematized on the basis of the hierarchical relations in concept. Words are organized hierarchically so that a conceptually high-level word (broader term) is positioned higher in the hierarchical structure, and a conceptually low-level word (narrower term) is positioned lower in the hierarchical structure. In the case where a major classified group expresses "disease", words related to "gastrointestinal diseases" are categorized in nodes of the first layer. Words related to "gastric diseases" are categorized in nodes of the second layer. Words related to "gastric ulcer" are categorized in nodes of the third layer. A position in the hierarchical structure (hereinafter, called "hierarchical position") in the thesaurus 19 is specified by a thesaurus code as a code given according to a predetermined rule. For example, the hierarchical positions of words related to "disease", "gastrointestinal diseases", "gastric diseases", and "gastric ulcer" are specified by thesaurus codes "A", "A-10", "A-10-20", and "A-10-20-30", respectively. "A" denotes the index of specifying the major classified group, and numerals such as "10", "20", and "30" are indices showing the hierarchical positions in the same hierarchy. The hyphen "-" denotes an index indicative of transition among levels. In the thesaurus 19, a specific word may have a plurality of broader terms, so that the hierarchical position can be specified by a plurality of thesaurus codes.

Another configuration may be employed. Concretely, with respect to one or more pieces of character information included in the initial search keyword group, for example, character information belonging to a level higher than a level of a keyword included in the initial search keyword group, that is, one or more pieces of character information of a higher concept is extracted from the thesaurus 19 and added to the search keyword group. After that, a keyword search using the resultant search keyword group is conducted. When a keyword search is performed in consideration of keywords of higher concept as well, the probability of detecting a desired image and report is increased.

In the foregoing embodiment, the case of supporting input of a radiological report has been described. The invention is not limited to the radiological report but can be applied to any reports as long as the invention supports input of reports describing images. For example, the invention can be applied to other medical information reports such as an incident report and a diagnosis report and, further, general reports including images such as a sales report and a report of countermeasures against claims.

In the foregoing embodiment, the predetermined number of classification items constructing single report structured data includes all of six classification items "image capture parameter", "region", "basic findings", "feature", "diagnosis", and "conclusive word". The invention is not limited to the embodiment. Another configuration employing one or more classification items out of the six classification items may be also employed.

In the foregoing embodiment, various entries are realized by various operations of a reading physician as the user on the operating unit 32 of the report input device 30. The invention is not limited to the embodiment. For example, various entries may be realized by receiving voice of the user by a microphone in the report input device and performing sound recognition. That is, various entries may be made in response to the various operations of the user including operation on the operating unit 32 of the user and sound production of the user.

In the foregoing embodiment, information stored in the input support DB 111 and the structured DB 213 is generated by analyzing an existing report by language processing. The invention is not limited to the embodiment. For example, information stored in the input support DB 111 and the structured DB 213 may be properly generated by manual operation. From viewpoint of facilitation in addition of metadata, preferably, information stored in the input support DB 111 and the structured DB 213 is automatically entered.

Although the server 100 and the terminals 10 to 50 are connected to each other via the network line NTW or the like in a hospital or the like so that data can be transmitted/received and the input support function using, as past knowledge, radiological reports accumulated in the hospital is provided, the invention is not limited to the embodiment. Alternatively, a database system 1A as shown in FIG. 29 may be also employed. In the database system 1A, a company or a specific hospital providing services of supporting entry of a radiological report has the server 100. A reading physician in any of hospitals accesses the server 100 via the Internet line IN or the like by using a terminal (for example, a report input device 30A) and can use the input support function including the retrieving function.

With such a configuration, the user can obtain visible information of a similar image and a related report of an instructed image by using the Internet capable of easily increasing an amount of information to be searched. Thus, the probability of obtaining a desired image and report further increases.

In this case, a company or the like having the server 100 may provide services for storing images, radiological reports, and the like of a hospital and the like.

In retrieval of a similar image and a related report using the Internet, there is a risk that personal information included in the attribute information attached to similar images and personal information described in related reports leaks. A representative example of the personal information is names (patient's name and the like).

Therefore, in the server 100, after a predetermined kind of personal information is deleted from the data of a detected similar image and a detected related report, the information related to the similar image and the related report may be provided for the terminal 30. Thus, the server 100 functions as a deleting unit regarding the previously mentioned predetermined kind of personal information that is deleted. As a method of recognizing the predetermined kind of personal information, for example, character information belonging to the predetermined kind of classification item "patient's name" is recognized as the predetermined kind of personal information. The character information of the personal information recognized can be easily erased.

With such a configuration, the personal information can be prevented from being leaked to a wide range.

In the foregoing embodiment, various operations are performed in the server 100 in response to an entry of the user in the report input device 30. The invention is not limited to the embodiment. For example, the functions of the report input device 30 and the server 100 may be performed by a single computer. In the report input device 30, only by various entries of the user, image data of the information retrieving function and a retrieval parameter are designated by the image designating unit by having the image data and the retrieval parameter may be substantially designated by the control unit 120 of the server 100, wherein the control unit 120 is part of the image designating unit.

Although the data of a similar image and a related report is retrieved by using the image data to be interpreted as a start point in the foregoing embodiment, the image data as a start point may be also determined as follows.

Figure 30:
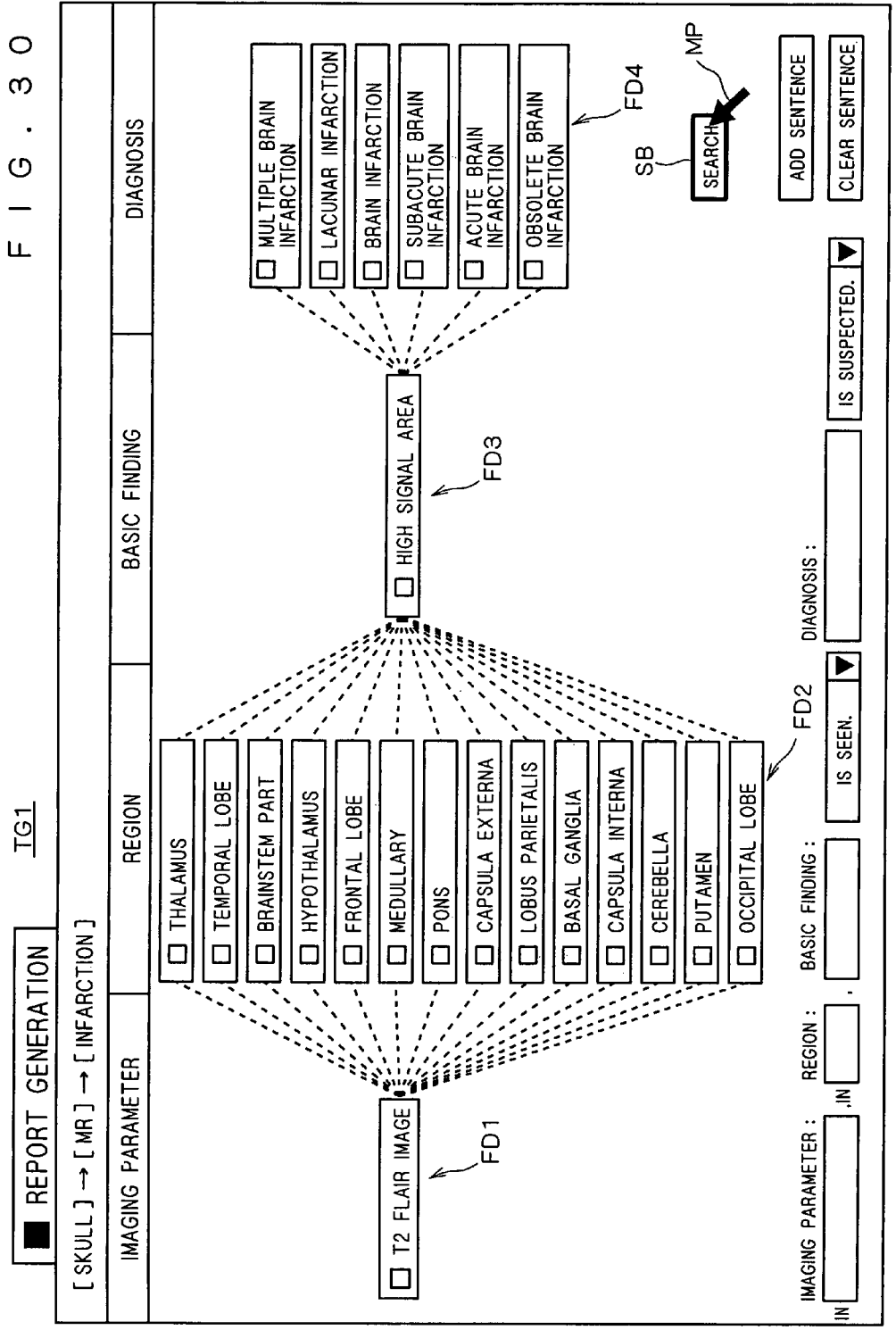
FIG. 30 is a diagram illustrating input support template display in the modification.

FIG. 30 is a diagram showing an input support template TG1 of a modification. In the input support template TG1, like the input support template TP2 of the foregoing embodiment, groups FD1 to FD4 each made of one or more words and phrases are displayed for the items "imaging parameter", "region", "basic finding", and "diagnosis", respectively. Further, a search button SB is added.

The search button SB is a button for retrieving image data as a start point in retrieval of the data of a similar image and a related report. When the user adjusts the mouse pointer MP onto the search button SB by properly operating the mouse and clicks the left button of the mouse (left click), a dialog box (search dialog) DG1 for determining search conditions as shown in FIG. 31 is displayed below the input support template TG1 (that is, around the remark display area A6).

In the search dialog DG1, by designating words and/or phrases for the items "imaging parameter", "region", "basic finding", and "diagnosis", combinations of the items "imaging parameter", "region", "basic finding", and "diagnosis" and words and/or phrases belonging to the items can be designated as search conditions.

The search conditions in the search dialog DG1 can be designated by adjusting the mouse pointer MP on a desired word or phrase included in the groups FD1 to FD4 displayed in correspondence with the items on the input support template TG1 and performing selecting operation (left click) in a state where the search dialog DG1 is displayed. FIG. 31 shows a state where, for example, the search dialog DG1 is displayed and, in the input support template TG1, the search conditions are designated that the phrase "T2 flair image" is associated with the item "imaging parameter", the phrase "temporal lobe" is associated with the item "region", the phrase "high signal area" is associated with the item "basic finding", and the phrase "lacunar infarction" is associated with the item "diagnosis".

Figure 32:
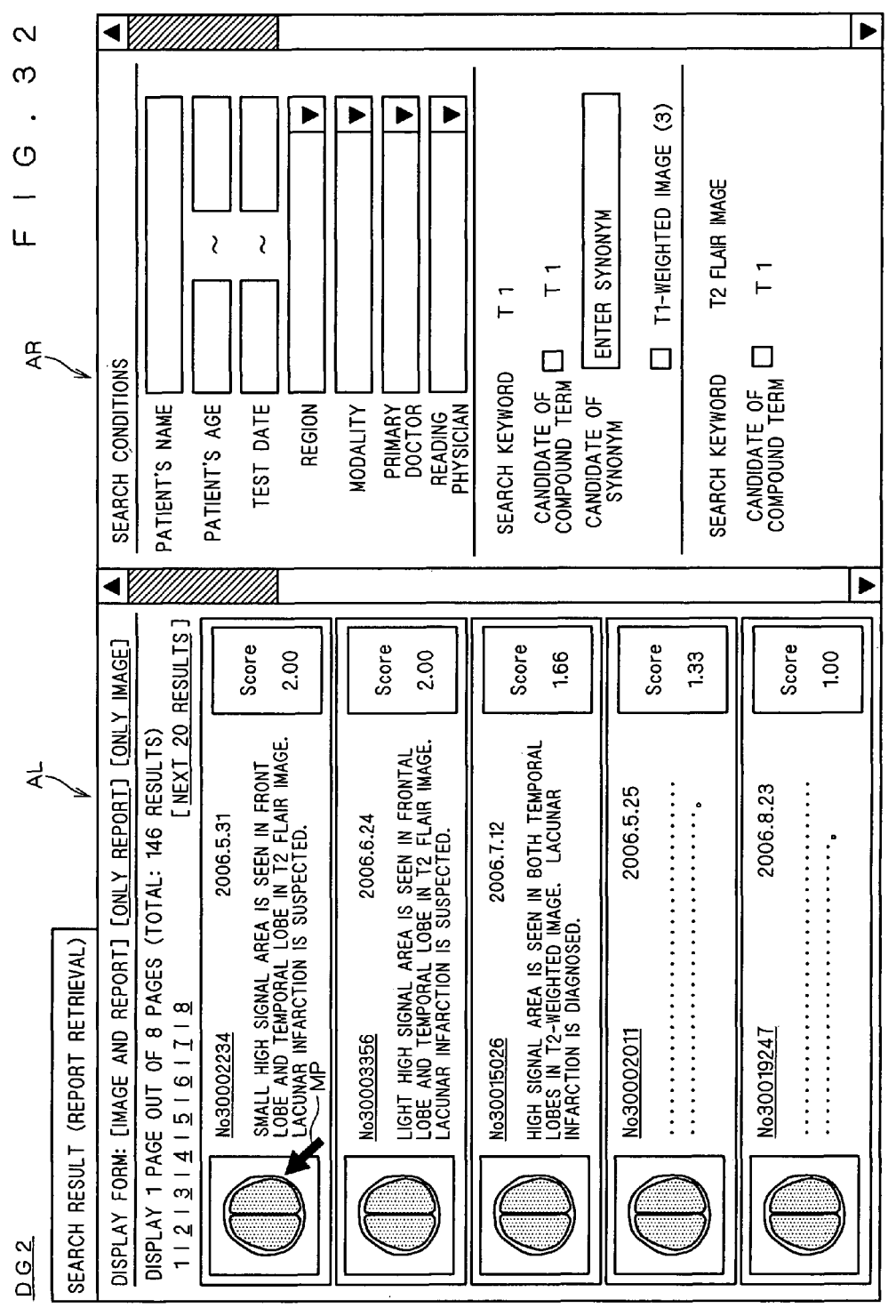

After designating the search conditions, when the user adjusts the mouse pointer MP on the search button SB2 and performs depressing operation (left click), the structured DB 213 is searched and one or more pieces of single report structured data to which attribute values completely or partly matching the designated search conditions are given is detected. In an area extending from the generation support information display area A5 to the remark display area A6, a dialog box (search result display dialog) DG2 displaying a search result as shown in FIG. 32 is displayed.

The search result display dialog DG2 is constructed mainly by an area (search result display area) AL displaying a search result on the left side, and an area (re-search condition display area) AR displaying search conditions for performing re-search on the right side.

To the search result display area AL, the data of images and remarks of one or more single report structured data to which attribute values completely or partly matching the search conditions designated in the search dialog DG1 (FIG. 31) is visibly output. FIG. 32 shows a state where 146 pieces of single report structured data are detected, and the data of images and remarks of five pieces out of 146 pieces of the single report structured data is visibly output in order from the top. In the rightmost area of the search result display area AL, a score indicative of coincidence between each piece of the single report structured data and the search conditions is shown. For example, in decreasing order of score, the detected single report structured data is visibly output to the space in order from top.

By referring to the images displayed in the search result display area AL and the remarks, the user can properly determine an image as a start point of retrieval of the data of a similar image and/or a related report. Concretely, when the user adjusts the mouse pointer MP onto a desired image as one of the images displayed in the search result display area AL and clicks the right button of the mouse, the command list CL1 as shown in FIG. 20 appears. For example, when the command "retrieval of similar image" or the like in the list CL1 is designated, the image data of a desired image on which the mouse pointer MP is adjusted as one of the images displayed in the search result display area AL is determined as image data of a retrieval reference image as a start point of retrieval of the data of a similar image and a related report. By a process similar to that of the embodiment, a search result display screen as shown in FIG. 23 is displayed. In the retrieval of data of a similar image and a related report, an image which was already tested is designated as the retrieval reference image. Consequently, one or more pieces of character information directly and/or indirectly associated with image data of the retrieval reference image in the structured DB 213 is/are designated and used as a search keyword group.

In the search result display area AL, numbers are assigned on the right side of the images. The numbers express the file names storing original image data in the image DB 212. By adjusting the mouse pointer MP on desired number and performing designated operation (left click), a link is established so that the original image data is displayed visibly largely.

On the other hand, in the re-search condition display area AR, the search conditions of a re-search can be determined so as to properly narrow candidates of images which can become a start point of retrieval of the data of a similar image and/or a related report and display the candidates in the search result display area AL. As shown in FIG. 32, in the re-search condition display area AR, to the conditions designated by the search dialog DG1 (FIG. 31), other conditions can be added with respect to items such as "patient's name", "patient's age", "test date", "region", "modality", "primary doctor", "reading physician", and the like. To the search keywords, conditions regarding variations of words such as a compound term, synonym, and the like (for example, a compound term and synonym to be considered for words in a search) can be also properly added. Although not shown, when the mouse pointer MP is adjusted onto a re-search button provided at the bottom of the re-search condition display area AR and depressing operation (left click) is performed, the structured DB 213 is searched, and one or more pieces of single report structured data to which attribute values completely or partly matching the re-designated search conditions (re-search conditions) are given is/are detected. The display in the search result display area AL is updated.

By employing such a configuration, under the condition designated in the search dialog DG1 (FIG. 31), when narrowing of candidates of an image which can become the start point of retrieval of the data of a similar image and/or a related report is insufficient, by properly performing re-search, the user can determine image data as the start point of retrieval of data of a similar image and/or a related report more quickly and easily. That is, entry of a search condition in retrieval of data of a similar image and/or a related report is further facilitated.

While the invention has been shown and described in detail, the foregoing description is in all aspects illustrative and not restrictive. It is therefore understood that numerous modifications and variations can be devised without departing from the scope of the invention.

What is claimed is:

1. A database system comprising:
a computer comprising a central processing unit;
an association information database in communication with said central processing unit that accumulates and stores 1) words or phrases constructing a report, 2) one or more pieces of image data related to said report, and 3) a plurality of association information in which said words or phrases constructing said report and said one or more pieces of image data related to said report are associated with each other;
an image designating unit in response to an operation of a user, for designating a first set of one or more pieces of image data associated with said words or phrases belonging to at least part of a predetermined number of classification items to which said words or phrases belong;
a server comprising an image detecting unit for detecting a second set of one or more pieces of image data different from but similar to said first set of one or more pieces of image data designated by said image designating unit, wherein said image detecting unit performs the following process among said one or more pieces of image data stored in said association information database:
1) performing a keyword search of said one or more pieces of image data stored in said association information database using a search keyword group formed by said words or phrases associated with said first set of one or more pieces of image data designated by said image designating unit, and
2) detecting image data from said keyword search that is consistent with said search keyword group, wherein said detected image data constitutes said second set of one or more pieces of image data and is associated with words or phrases that are consistent with said search keyword group; and
a terminal device connected to said server via an Internet line so that data can be transmitted/received to/from said server, wherein, in response to an operation of a user to said terminal device, said image designating unit designates said one or more pieces of image data with which said words or phrases belonging to at least a part of said predetermined number of classification items is/are associated,
said server has a transmitting unit for transmitting said one or more pieces of image data detected by said image detecting unit to said terminal device via said Internet line, and
said terminal device has an output unit for visibly outputting said one or more pieces of image data transmitted from said transmitting unit.

2. The database system according to claim 1, further comprising:
a report database that stores report information in which said report and said one or more pieces of image data are associated with each other;
a character information extracting unit for extracting said words or phrases constructing said report by performing language analysis on said report included in said report database; and
a storage controlling unit for constructing said association information database by storing-said words or phrases-constructing said report extracted by said character information extracting unit and said one or more pieces of image data related to said report so as to be associated with each other.

3. The database system according to claim 1, wherein said words or phrases constructing said association information include attribute information added to said one or more pieces of image data related to said report included in said association information database.

4. The database system according to claim 3, wherein said attribute information includes at least one piece of information of patient's identification, age, sex, a modality, a test region, a reading physician, and a primary doctor.

5. The database system according to claim 1, further comprising a dictionary database that stores said words or phrases and at least one or more pieces of association character information having a predetermined relation with said words or phrases so as to be associated with each other, wherein said keyword search includes a process of extracting, from said dictionary database, one or more pieces of association character information having said predetermined relation with said words or phrases included in said search keyword group and adding said at least one or more pieces of association character information extracted from said dictionary database to said search keyword group.

6. The database system according to claim 5, wherein said predetermined relation includes at least one of a near-synonym, a synonym, and a related term.

7. The database system according to claim 5, wherein said predetermined relation includes hierarchical relations in concept of said words or phrases, and
said keyword search includes a process of extracting one or more of said words or phrases having concept higher than one or more of said words or phrases included in said search keyword group from said dictionary database and adding said words or phrases extracted from said dictionary database to said search keyword group.

8. The database system according to claim 1, wherein said predetermined number of classification items include at least one of items of an imaging parameter, a region, a basic finding, a feature, a diagnosis, and a conclusive word.

9. The database system according to claim 1, wherein said keyword search includes a process of selectively employing, as said search keyword group, said words or phrases belonging to a part of said predetermined number of classification items, in said words or phrases associated with one or more image data designated by said image designating unit.

10. The database system according to claim 1, further comprising an item designating unit for designating at least a part of said predetermined number of classification items in response to an operation of a user, wherein said keyword search includes a process of selectively employing, as said search keyword group, said words or phrases belonging to a part of said predetermined number of classification items designated by said item designating unit, in said words or phrases associated with one or more image data designated by said image designating unit.

11. The database system according to claim 1, wherein said report included in said association information database include a radiological report.

12. The database system according to claim 1, wherein said server further comprises a deleting unit for deleting a predetermined kind of personal information from said one or more pieces of image data detected by said image detecting unit, and said transmitting unit transmits said one or more pieces of image data from which said predetermined kind of personal information is deleted by said deleting unit to said terminal device via said Internet line.

* * * * *